(12) United States Patent
Steele

(10) Patent No.: US 10,399,843 B2
(45) Date of Patent: Sep. 3, 2019

(54) PROGRAMMABLE WIRELESSLY-ACTIVATED AND CONTROLLED PORTABLE HYDRATION SYSTEMS, DEVICES, COMPONENTS AND METHODS

(71) Applicant: Matthew J. Steele, Blonay (CH)

(72) Inventor: Matthew J. Steele, Blonay (CH)

( * ) Notice: Subject to any disclaimer, the term of this patent is extended or adjusted under 35 U.S.C. 154(b) by 0 days.

(21) Appl. No.: 16/194,376

(22) Filed: Nov. 18, 2018

(65) Prior Publication Data

US 2019/0152760 A1 May 23, 2019

Related U.S. Application Data

(63) Continuation of application No. 15/720,059, filed on Sep. 29, 2017, now Pat. No. 10,179,726.

(60) Provisional application No. 62/402,336, filed on Sep. 30, 2016.

(51) Int. Cl.
| | |
|---|---|
| *B67D 1/12* | (2006.01) |
| *B67D 1/00* | (2006.01) |
| *B67D 1/08* | (2006.01) |
| *B67D 1/10* | (2006.01) |
| *A62B 18/08* | (2006.01) |

(52) U.S. Cl.
CPC .......... *B67D 1/1243* (2013.01); *A62B 18/086* (2013.01); *B67D 1/0005* (2013.01); *B67D 1/0888* (2013.01); *B67D 1/10* (2013.01); *B67D 2001/0097* (2013.01); *B67D 2210/00131* (2013.01)

(58) Field of Classification Search
CPC .... A61M 1/00; A61F 5/44; A61B 5/00; A61B 18/12; F04B 49/06; G05D 7/06
USPC ....... 340/12.29; 600/549; 604/347, 319, 326
See application file for complete search history.

(56) References Cited

U.S. PATENT DOCUMENTS

| | | | | |
|---|---|---|---|---|
| 7,141,043 | B2* | 11/2006 | Harvie | A61F 5/451 604/347 |
| 8,594,573 | B2* | 11/2013 | Miettinen | A61B 5/0006 370/478 |
| 9,244,449 | B2* | 1/2016 | Tennyson | G05B 19/02 |
| 9,342,996 | B2* | 5/2016 | King | G09B 23/28 |
| 9,722,412 | B2* | 8/2017 | Martins | G06F 1/28 |
| 9,902,605 | B2* | 2/2018 | Lux | B67D 1/10 |
| 10,179,726 | B2* | 1/2019 | Steele | A62B 18/086 |
| 10,231,567 | B2* | 3/2019 | Perrelli | A47J 31/005 |
| 2008/0234600 | A1* | 9/2008 | Marsh | A61B 5/01 600/549 |
| 2016/0090981 | A1* | 3/2016 | Ryan | F04B 49/065 700/283 |
| 2017/0319260 | A1* | 11/2017 | Ngo | A61B 18/1206 |

* cited by examiner

*Primary Examiner* — Nam V Nguyen
(74) *Attorney, Agent, or Firm* — Woods Patent Law, P.A.

(57) ABSTRACT

Described herein are various embodiments of systems, devices, components and methods for providing hydration to a user from a fluid reservoir or bladder, where the fluid is provided on demand by the user activating and controlling a user interface that communicates wirelessly with a control assembly operably connected to a pump and the fluid reservoir.

17 Claims, 8 Drawing Sheets

PROGRAMMABLE WIRELESSLY-ACTIVATED AND CONTROLLED PORTABLE HYDRATION SYSTEMS, DEVICES, COMPONENTS AND METHODS

PRIORITY, BENEFITS AND CROSS-REFERENCES TO RELATED APPLICATIONS

This patent application is a continuation application of parent U.S. patent Ser. No. 10/179,726 issued on Jan. 15, 2019 entitled "Programmable Wirelessly-Activated and Controlled Portable Hydration Systems, Devices, Components and Methods " to Matthew J. Steele ("the '726 parent patent"), and claims priority and other benefits therefrom. The '726 parent patent is hereby incorporated by reference herein, in its entirety, to provide continuity of disclosure. This patent application also claims priority and other benefits through the '726 parent patent to U.S. Provisional Patent Application Ser. No. 62/402,336 to Matthew J. Steele filed on Sep. 30, 2016, entitled (hereafter "the '336 patent application"). The '336 patent application is also hereby incorporated by reference herein, in its entirety, to provide continuity of disclosure.

FIELD OF THE INVENTION

Various embodiments of the invention described herein relate to the field of systems, devices, components, and methods for wirelessly and controllably delivering hydration fluids to a user.

BACKGROUND

Various printed publications, patents and patent applications disclosing subject matter relating directly or indirectly to the methods, systems, devices and components disclosed herein include, but are not limited to, the following:
  U.S. Pat. No. 4,150,681 to Howarth entitled "Visor mounted washer for goggles"
  U.S. Pat. No. 4,541,657 to Smyth entitled "Quick release hose coupling"
  U.S. Pat. No. 4,526,298 to Boxer et al. entitled "Sport hydration system"
  U.S. Pat. No. 4,629,098 to Eger entitled "Portable liquid dispenser"
  U.S. Pat. No. 4,815,635 to Porter entitled "Cyclist water supply apparatus"
  U.S. Pat. No. 5,062,591 to Runkel entitled "Pressurized potable beverage drinking system"
  U.S. Pat. No. 5,201,442 to Bakalian entitled "Remote control water device"
  U.S. Pat. No. 5,316,041 to Ramacier Jr, et al. entitled "Quick connection coupling valve assembly", May 31, 1994, assigned to Colder Product Co.
  U.S. Pat. No. 5,378,024 to Kumagai, et al. entitled "Quick connector"
  U.S. Pat. No. 5,571,260 to Krug entitled "Portable liquid container and dispenser system"
  U.S. Pat. No. 5,645,404 to Zelenak et al. entitled "Personal fluid dispensing device"
  U.S. Pat. No. 5,735,440 to Regalbuto entitled "Bicycle mounted squirt gun and fluid dispensing apparatus"
  U.S. Pat. No. 5,755,368 to Bekkedahl entitled "Liquid dispensing apparatus for bicyclists and skaters"
  U.S. Pat. No. 5,975,387 to Gleason, et al. entitled "Bladder frame backpack
  U.S. Pat. No. 6,039,305 to Hoskins, et al. entitled "Bite valve for hydration bladder"
  U.S. Pat. No. 6,070,767 to Gardner, et al. entitled "Personal hydration system with an improved mouthpiece"
  U.S. Pat. No. 6,105,827 to Rowan entitled "Beverage dispensing helmet apparatus"
  U.S. Pat. No. 6,283,344 to Bradley entitled "Hands free personal hydration delivery system"
  U.S. Pat. No. 6,364,168 to Gardner, et al. entitled "Personal hydration system with an improved mouthpiece"
  U.S. Pat. No. 6,497,348 to Forsman, et al. entitled "Hydration system with improved fluid delivery system"
  U.S. Pat. No. 6,675,998 to Forsman, et al. entitled "Hydration system with improved fluid reservoir"
  U.S. Pat. No. 6,749,090 to Bailey entitled "Dual bladder sports hydration system"
  U.S. Pat. No. 6,892,915 to Mares entitled "Pack frame assembly and hydration systems incorporating the same"
  U.S. Pat. No. 6,908,015 to Choi, et al. entitled "Personal hydration system with component connectivity"
  U.S. Pat. No. 6,981,613 to Kamisugi entitled "Portable pressurized liquid storage system"
  U.S. Pat. No. 7,007,502 to Kreutzmann entitled "In-car hydration systems"
  U.S. Pat. No. 7,063,243 to Forsman, et al. entitled "Hydration system with improved fluid reservoir"
  U.S. Pat. No. 7,070,075 to Forsman, et al. entitled "Hydration system with improved fluid reservoir"
  U.S. Pat. No. 7,073,688 to Choi, et al. entitled "Personal hydration system with component connectivity"
  U.S. Pat. No. 7,201,299 to Forsman, et al. entitled "Waist-mounted hydration system"
  U.S. Pat. No. 7,806,300 to Noell, et al. entitled "Hydration system"
  U.S. Pat. No. 7,971,549 to Skillern, et al. entitled "Hydration system for kayak integration"
  U.S. Pat. No. 8,083,105 to Reichert, et al. entitled "Pressurized fluid delivery system"
  U.S. Pat. No. 8,267,283 to Staton entitled "Personal hydration system"
  U.S. Pat. No. 8,276,785 to Wheatley, et al. entitled "NBC/CBRNE personal hydration system"
  U.S. Pat. No. 8,408,425 to Lien entitled "Hydration device"
  U.S. Pat. No. 8,469,226 to Davies, et al. entitled "Drink containers"
  U.S. Pat. No. 9,375,742 to Yokan entitled "Motorized hydration system"
  U.S. Patent Publication No. 2006/0180154 to Stone entitled "Apparatus for attaching a hydration device to a full face helmet"
  U.S. Patent Publication No. 2016/0090981 to Ryan entitled "Portable hydration system usable with a protective helmet"

The dates of the foregoing publications may correspond to any one of priority dates, filing dates, publication dates and issue dates. Listing of the above patents and patent applications in this background section is not, and shall not be construed as, an admission by the applicants or their counsel that one or more publications shown in the above list constitute prior art in respect of the applicant's various inventions. All printed publications, patents and patent applications referenced above or otherwise herein are hereby incorporated by referenced herein, each in its respective entirety.

Portable hydration systems adapted to be worn, carried or otherwise made available to a user often comprise a bladder disposed in a backpack, a hydration bite valve, and a hydration hose extending between the bite valve and the bladder so that the user can suck water or other drinkable fluid from the bladder through the hydration hose and the hydration bite valve. Such hydration systems are typically configured so they may be employed in a substantially hands-free manner, and are often portable.

Motorcycling and motorcycle racing, bicycling and bicycle racing, and auto racing are activities where drivers or riders can become dehydrated, especially in long or endurance races or events that can last many hours. In fast moving races or events, it is imperative that the driver or rider keep his or her hands on the vehicle or bike controls at all times.

In such races and events, however, racers or participants routinely wear helmets for head protection. Routing a hydration hose through, around or under a helmet, and arranging a hydration bite valve in a position that remains comfortable and usable over a sustained period of time for a helmet-wearing user, can be difficult or impractical. Adjustment or tinkering with a hydration hose or bite valve during such events is often not an option. As a result, conventional portable hydration systems employing bite valves, hydration hoses and bladders are not well suited for use in such races or events.

To overcome the problems associated with conventional portable hydration systems employing hydration hoses and bite valves, a few electrical pump fluid delivery systems have been developed which are capable of delivering squirts of fluid to the mouth of a user over a distance of a few inches, where the distal end of a hydration hose is positioned near the mouth of the user, and where the user typically actuates the electrical pump using a hard-wired switch. However, some of these electrical pump fluid delivery systems require as much or more manual interaction by the user as conventional hydration systems. In addition, including electrical and electronic hardware in a hydration system to permit enhanced control of fluid delivery can be cumbersome and heavy to implement, and lead to reliability and cost problems, such as relays, wires or switches that are prone to failure.

What is needed is a portable hydration system that can be used with ease, that is comfortable and reliable, and that does not require regular or excessive adjustment to operate properly.

Upon having read and understood the Summary, Detailed Description and Claims set forth below, those skilled in the art will appreciate that at least some of the systems, devices, components and methods disclosed in the printed publications listed herein may be modified advantageously in accordance with the teachings of the various embodiments that are disclosed and described herein.

SUMMARY

In one embodiment, there is provided a portable wirelessly-controlled and activated hydration system comprising a first control assembly comprising a first wireless transceiver and at least a first computing device the first computing device comprising at least a first non-transitory computer readable medium configured to store first instructions executable by at least a first processor, a second control assembly comprising a user interface, a second wireless transceiver configured to transmit user control signals to the first wireless transceiver corresponding to one or more inputs provided by a user to the user interface, and at least a second computing device operably connected to the user interface and the second wireless transceiver, the second computing device comprising at least a second non-transitory computer readable medium configured to store second instructions executable by at least a second processor, a quick connect mechanism configured for rapid attachment to and disconnection from a fluid reservoir, a fluid input tube comprising first and second ends, the first end being attached to the quick connect mechanism, a fluid output tube comprising first and second ends, the second end being configured to deliver fluid to a mouth of a user, and a fluid pump operably connected to the first control assembly and comprising input and output ports, operation of the fluid pump being controlled by the first computing device, the input port of the fluid pump being operably connected to the second end of the input tube, the output port of the fluid pump being connected to the first end of the output tube, the pump being configured to pump fluid from the fluid reservoir through the fluid input tube, the pump and the fluid output tube to the mouth of the user, wherein the first instructions of the first computing device of the first control assembly are programmable and include instructions executable by the first computing device to control operation of the pump thereby, the second instructions of the second computing device of the second control assembly are programmable and include instructions executable by the second computing device corresponding to the user control signals, the second wireless transceiver is configured to transmit user control signals wirelessly to the first wireless transceiver for processing and execution by the first computing device thereby to control operation of the pump thereby, and the first and second control assemblies are configured to pair wirelessly and uniquely with one another to prevent interference or crosstalk with other undesired nearby wirelessly communicating devices.

Such an embodiment, and other embodiments, may include one or more of: the first control assembly further comprising a first power supply for electrically powering at least portions of the first control assembly; the second control assembly further comprising a second power supply for electrically powering at least portions of the second control assembly, the fluid reservoir being a hydration bladder; the user interface of the second control assembly being one of a push button, a mechanical switch, an electromechanical switch, a capacitive proximity switch, and an electronic switch; the fluid pump and the first control assembly being operably connected to and included in a portable hydration pack; the first instructions executed by the first processor including one or more of pump control instructions or portions thereof, pump on instructions, pump off instructions, pump rate instructions, pump duration instructions, and pump pulse width modulation instructions; the second instructions executed by the second processor including one or more of user control instructions or portions thereof, pump on instructions, pump off instructions, pump rate instructions, pump duration instructions, and pump pulse width modulation instructions, the first control assembly being configurable by a user to control one or more of a pressure at which fluid is delivered by the pump, a rate at which fluid is delivered by the pump, and a duration of time over which fluid is delivered by the pump when the user interface of the second control assembly is actuated by the user; the first control assembly further comprising an onboard potentiometer configurable by the user to control one or more of a pressure at which fluid is delivered by the pump, a rate at which the fluid is delivered by the pump, a duration of time over which fluid is delivered by the pump when the user interface of the second control assembly is actuated by the user; the second control assembly being configurable to send repeated pump-on commands to the first control assembly for a predetermined period of time after the user interface has been pressed; the first control assembly being configured to repeat listening commands for a predetermined period of time after the user interface has been pressed; one or more of the first control assembly, the second control assembly, and the pump including one or more of voltage surge spike protection, EMI suppression, and reverse polarity protection; one or more of the first processor and the second processor comprising a microprocessor, a controller, a micro-controller, and a CPU; at least one of the first and second control assemblies being configured to enter a power-saving sleep mode after a predetermined period of time has passed with no user inputs or activity; at least one of the first and second control assemblies being configured to wake up from the power-saving sleep mode when the user provides an input to the user interface or initiates a power reset in the first or second control assemblies; and one or more light emitting diodes being operably connected to at least one of the first and second control assemblies, the one or more LEDs being configured to provide the user with visual feedback and information regarding control assembly pairing status, pairing signal strength, and power status.

In another embodiment, there is provided a method of pairing first and second control assemblies in a portable wirelessly-controlled and activated hydration system, the first control assembly comprising a first wireless transceiver and at least a first computing device the first computing device comprising at least a first non-transitory computer readable medium configured to store first instructions executable by at least a first processor, the second control assembly being separate from the first control assembly, the second control assembly comprising a user interface, a second wireless transceiver configured to transmit user control signals to the first wireless transceiver corresponding to one or more inputs provided by a user to the user interface, and at least a second computing device operably connected to the user interface and the second wireless transceiver, the second computing device comprising at least a second non-transitory computer readable medium configured to store second instructions executable by at least a second processor, the first assembly being configured for operable connection to and control of a fluid pump, wherein the first and second wireless transceivers are configured to permit the first and second control assemblies to communicate wirelessly with one another, the method comprising pairing the first control assembly and second control assembly uniquely to one another thereby to avoid crosstalk or interference with other undesired nearby wirelessly communicating devices.

Such a method, and other methods, may further comprise uniquely pairing the first control assembly with multiple second control assemblies, and/or uniquely pairing the second control assembly with multiple first control assemblies.

Further embodiments are disclosed herein or will become apparent to those skilled in the art after having read and understood the specification and drawings hereof.

BRIEF DESCRIPTION OF THE DRAWINGS

Different aspects of the various embodiments will become apparent from the following specification, drawings and claims in which:

The drawings are not necessarily to scale. Like numbers refer to like parts or steps throughout the drawings.

DETAILED DESCRIPTIONS OF SOME EMBODIMENTS

Described herein are various embodiments of systems, devices, components and methods for providing hydration to a user from a fluid reservoir or bladder, where the fluid is provided on demand by the user activating and controlling a user interface that communicates wirelessly with a control assembly operably connected to a pump and the fluid reservoir. The control assembly is operably and programmably connected to the fluid pump, which in turn is connected to the fluid reservoir to pump fluid therefrom to a mouth of a user upon demand thereby. Other embodiments encompassing use of a similar system for portable, stationary, bilge, sump pump, and handicapped person applications are also described and contemplated.

Figure 1:
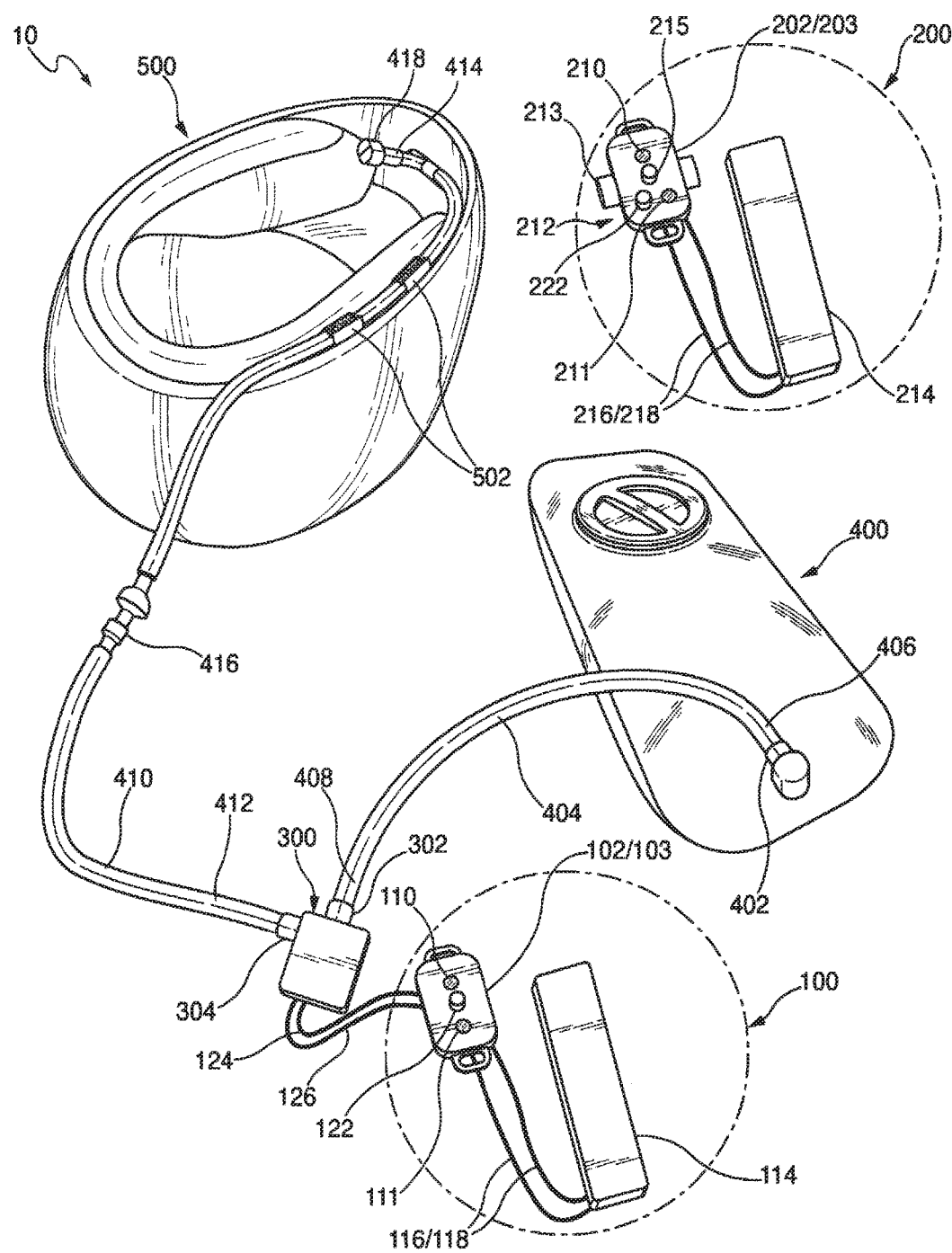
FIG. 1 shows one embodiment of a portable hydration system 10.

Referring now to FIG. 1, there is shown one embodiment of a portable wirelessly-controlled and activated hydration system 10. In the embodiment shown in FIG. 1, system 10 comprises first control system 100, second control system 200, fluid pump 300, fluid reservoir or hydration bladder 400, and helmet 500. In many applications, fluid reservoir or hydration bladder 400 is contained or held in a backpack, waist-pack or similar device for carrying by a user (not shown in the Figures). Note that in some embodiments, not all the foregoing elements or components are required or need be present.

In the embodiment shown in FIG. 1, first control system 100 comprises first control assembly 102, enclosure 103 for first control assembly 102, first LEDs/visual indicators 110/111, first power supply 114, first power supply positive and negative wires and connections 116/118, and first control assembly pairing button 122. First control assembly 102 is operably connected to and electrically powered by power supply 114, which may comprise one or more batteries, or any other suitable source of portable or stationary electrical energy, such as DC or AC electrical power.

First control system 100 is operably connected to fluid pump 300, which in turn is operably connected to hydration or fluid reservoir or balder 400 and helmet 500 by means of hydration hoses 404 and 410. Hydration hose 404 is connected to input port 302 of pump 300, and comprises first and second ends 406 and 408, and has optional quick-connect mechanism 402 attached to end 406 for quick connection and release from bladder 400. Hydration hose 410 comprises first end 412, second end 414, and nozzle/mouthpiece 418, and is connected to output port 304 of pump 300, and provides fluid from bladder 400 pumped by pump 300 to a user wearing helmet 500. Hose 410 may be routed through helmet cuffs 502 mounted inside or outside helmet 500, and may also feature an optional second quick-connect and release mechanism 416 to permit a user wearing helmet 500 to quickly attach to and release from the other components of hydration system 10.

Non-limiting examples of pumps 300 suitable for use in connection with at least some of the embodiments shown in FIGS. 1-7(*b*) hereof are pump model numbers AD10B, AD103, AD400, manufactured by Shenzhen Giant Electric Tech Inc. of the People's Republic of China. These pumps are all centrifugal, operate at 12 Volts DC, are single stage, have ABS plastic housings, provide maximum flow rates around 300 to 400 liters/hour, weigh around 60-70 grams, and have noise levels less than around 40 dB. Note that least some of the foregoing Shenzhen Giant Electric Tech Inc. pumps are not suitable for applications where pulse width modulation (PWM) control schemes are employed by systems 100 or 200. In PWM applications, other types of pumps 300 can be used. Still other types of suitable pumps are also contemplated, such as those which operate under AC power.

In the embodiment shown in FIG. 1, second control system 200 comprises user interface 212, which in turn comprises second control assembly 202, enclosure 203 for second control assembly 202, second LEDs/visual indicators 210/211, second power supply 214, second power supply positive and negative wires and connections 216/218, and second control assembly pairing button 222. Second control assembly 202 is operably connected to and electrically powered by power source 214, which may comprise one or more batteries, or any other suitable source of portable or stationary electrical energy, such as DC or AC electrical power. Switch or control 215 permits a user to activate or deactivate wirelessly, as the case may be, or to otherwise control operation or programming of, first control system 100 and/or pump 300. Note that the embodiment of second control system 200 shown in FIG. 1 differs from the embodiment of second control system 200 shown in FIG. 3 in the respect that second control system 200 shown in FIG. 1 has user interface 212 and switch 215 incorporated into second control assembly 202 and enclosure 203. In second control system 200 shown in FIG. 3, however, user interface 212 and switch 215 are located separate from second control assembly 202 (but remain operably connected thereto).

In one embodiment, user interface 212 is attached to a handlebar or other type or component of a vehicle that is being operated by the user by means of user interface attachment mechanism 213, which may comprise bracket(s), one or more Velcro straps, an adhesive, bolts and nuts, or any other suitable means of attaching user interface 212 to the vehicle that is being operated by the user or the vehicle component. In another embodiment, where for example the user is a runner or skier, user interface 212 can be configured to be hand-held, or to be attached or incorporated into, by way of illustrative non-limiting example, the user's belt, wrist, glove, mitten, finger ring, clothing, sleeve, ski pole, or other portable or wearable device or clothing article.

Figure 2:
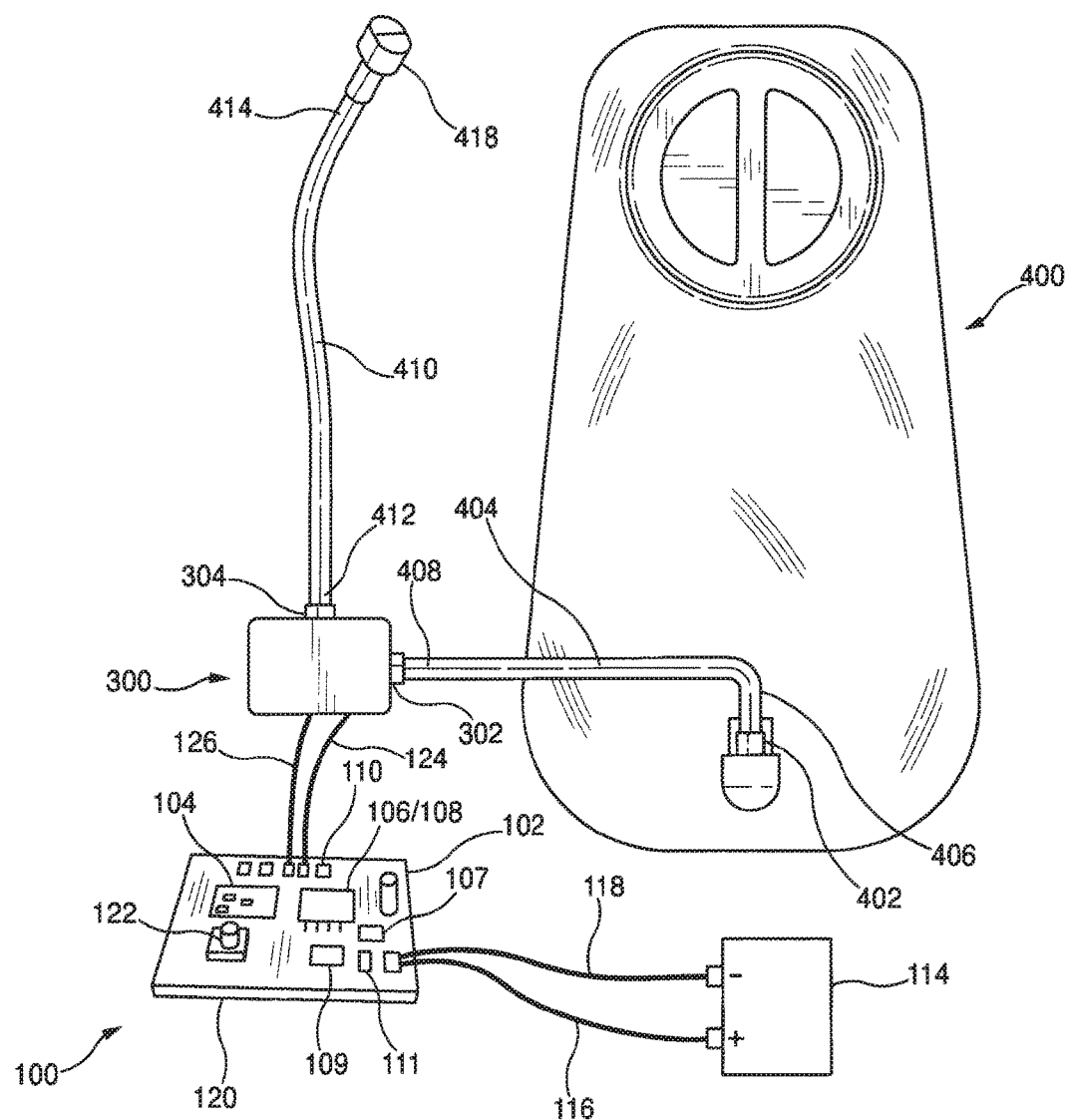
FIG. 2 shows one embodiment of first control system 100 and various components associated therewith.
Figure 3:
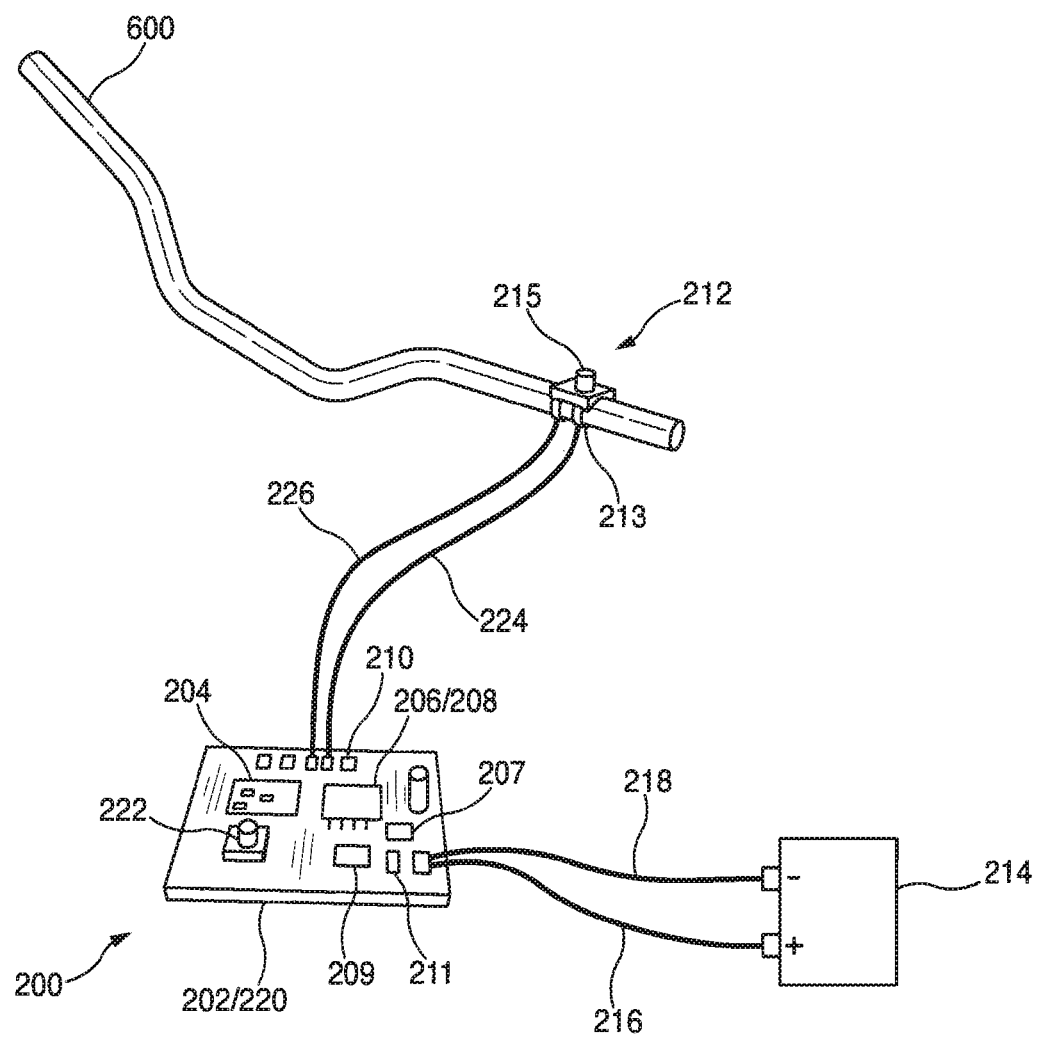
FIG. 3 shows one embodiment of second control system 200 and various components associated therewith.

FIGS. 2 and 3 show further details of the embodiments of first control system 100 and second control system 200 shown in FIG. 1, respectively, and various components associated therewith.

In FIG. 2, a conventional athletic activity hydration bladder 400 is shown connected to quick-connect mechanism 402. Such a quick-connect mechanism 402 can be employed, but other means of connecting to bladders or reservoirs 400 are also contemplated such as permanent or semi-permanent hydration hose connection mechanisms. In addition, types of fluid reservoirs 400 other than hydration bladders are also contemplated, such as portable or fixed or stationary fluid refillable bottles and containers.

In FIG. 2, and for illustrative purposes, first control system 100 is represented and shown without protective enclosure 103 surrounding first control assembly 102. First control assembly printed circuit board 120 is shown with various electronic and electrical components mounted thereon, such as first wireless transceiver 104, first computing device 106 and first processor 108, first LEDs/visual indicators 110/111, first voltage regulator 107, first potentiometer 109, and first pairing button, switch or control 122. First power supply 114 is operably connected to first control assembly printed circuit board 120 by wires or electrical conductors 116 and 118, while pump 300 is operably connected to first control assembly printed circuit board 120 by wires or electrical conductors 124 and 126. Pump inlet port 302 of pump 300 is operably connected by hose 404 to hydration balder or reservoir 400. Hydration hose 410 connects outlet port 304 of pump 300 to nozzle or mouthpiece 418, which is configured to be positioned near a user's mouth to receive fluid from reservoir 400 as pump 300 conveys fluid therefrom to the distal end 414 of hose 410. (As shown in FIG. 1, however, hose 410 may include an additional quick-connect mechanism 416, and distal end 414 may be attached to a helmet 500.) Nozzle or mouthpiece 418 may also be configured to focus a stream of water to the mouth of a user.

In FIG. 2, first control assembly includes printed circuit board 120 with the various electronic components listed above, including first computing device 106, which can comprise, by way of example, a processor, microprocessor, controller or CPU 108 comprising RAM and ROM memory, busses, and other components included in or connected to computer processors such as storage devices and so on. First computing device/first processor 106/108 is also operably connected to first wireless transceiver 104, which is configured to communicate wirelessly with second wireless transceiver 204 of second control system 200. Pairing button 122 can be employed for a user to change communication channels employed by wireless transceiver 104, more about which is said below. Potentiometer 109 can be employed to adjust or change the pump flow duration of pump 300. Voltage regulator 107 allows first control assembly 102 to operate across a range of different or varying input voltages delivered by power supply 114. LEDs/visual indictors 110 and 111 can be configured to indicate to a user power status and connection status/signal reception between control system 100 and control system 200. As noted above, power supply 114 may comprise a battery pack, or may comprise a vehicle or any other suitable type of AC or DC power. Pump 300, first control assembly 102, and power supply 114 may all or in any combination be contained in a protective enclosure.

In FIG. 3, and for illustrative purposes, second control system 200 is represented and shown without protective enclosure 203 surrounding second control assembly 202. Second control assembly printed circuit board 220 is shown with various electronic and electrical components mounted thereon, such as second wireless transceiver 204, second computing device 206 and second processor 208, second LEDs/visual indicators 210/211, second voltage regulator 207, second potentiometer 209, second LEDs/visual indicators 210/211, and second pairing button, switch or control 222. Second power supply 214 is operably connected to second control assembly printed circuit board 220 by wires or electrical conductors 216 and 218, while user interface 212 is operably connected to second control assembly printed circuit board 220 by wires or electrical conductors 224 and 226 (although wireless connection between user interface 212 and second control system/second control assembly 202 is also contemplated).

Second control assembly 102 includes second printed circuit board 220 with the various electronic components listed above, including second computing device 206, which can comprise, by way of example, a processor, microprocessor, controller or CPU 208 comprising RAM and ROM memory, busses, and other components typically included in or connected to computer processors such as storage devices and so on. Second computing device/second processor 206/208 is also operably connected to second wireless transceiver 204, which is configured to communicate wirelessly with first wireless transceiver 104 of first control system 100, and optionally with user interface 212 as described above. Pairing button 222 can be employed for a user to change communication channels employed by wireless transceiver 204 and/or wireless transceiver 104. Voltage regulator 207 allows second control assembly 202 to operate across a range of different or varying input voltages delivered by power supply 214. LEDs/visual indicators 210 and 211 can be configured to indicate to a user power status and connection status/signal reception between second control system 200 and first control system 100. As noted above, power supply 214 may comprise a battery pack, or may comprise a vehicle-mounted power supply, or any other suitable source of AC or DC power. System 200 and power supply 214 may all or in any combination be contained in a protective enclosure.

Continuing to refer to FIG. 3, user interface 212 is shown attached to handlebar 600 of a motorcycle or bicycle by means of attachment mechanism 213. User interface 212 is mounted and positioned to provide easy access to a finger or hand of a user so that switch or control 215 may be activated or deactivated easily and essentially hands-free by a user while the bicycle or motorcycle is being operated. User interface 212 may also be mounted on steering wheel of a vehicle or any other portion of a vehicle being piloted by a user. In FIG. 3, and to reduce system costs and expense, the hardware mounted on second control assembly printed circuit board 220 may be identical to that of first control assembly printed circuit board 120. In one embodiment, activation of button/switch 215 by the user causes second control assembly 202 to send a series of repeating commands through wireless transceiver 204 to first control assembly 102 to which it is paired. Second control assembly printed circuit board may be enclosed in a protective enclosure 203 (not shown in FIG. 3, but shown in FIG. 1).

The components of system 10 shown in FIGS. 1, 2 and 3 are configured to operate together so that when a user presses button, switch or control 215 second control assembly 202 sends a repeating series of "pump-on" commands to pump 300 via second wireless transceiver 204 to first wireless transceiver 104 and first control assembly 102 to which it has been paired. When first control assembly 102 receives such "pump-on" commands, pump 300 is actuated by first computing system/first processor 106/108 to pump fluid from reservoir 400 to nozzle or mouthpiece 418. In one embodiment, pump 300 is electrically powered by first power supply 114 via electrical conductors 116/118 and 124/126, and via voltage regulator 107.

In some embodiments, pulse width modulation (PWM) is employed by first computing system/first processor 106/108 to finely control the delivery and timing of electrical current to pump 300 using programmable and/or stored software settings. In some embodiments, stored or programmed PWM settings can be selected by a user according to the flow rate, pressure, fluid volume, and duration of fluid delivery that the user desires. For example, first processor 108 may be configured by the user to deliver fluid for a predetermined and selected period of time after switch 215 has been pressed by the user, with fluid delivery being terminated after the predetermined period of time has passed. Alternatively, first processor 108 may be configured by the user to deliver fluid continuously while button or switch 215 is being pressed, and to stop delivering fluid after button or switch 215 has been released. The user may also change the pressure or rate at which fluid is being delivered by system 10. Other types of changes or controls regarding fluid delivery are also contemplated to be adjustable by a user, such as manual hardware adjustment by a user of potentiometer 109 to change fluid flow rate. In some embodiments where PWM is used to control the operation of pump 300, it is better to vary the current delivered to pump 300 rather than the voltage.

Figure 4:
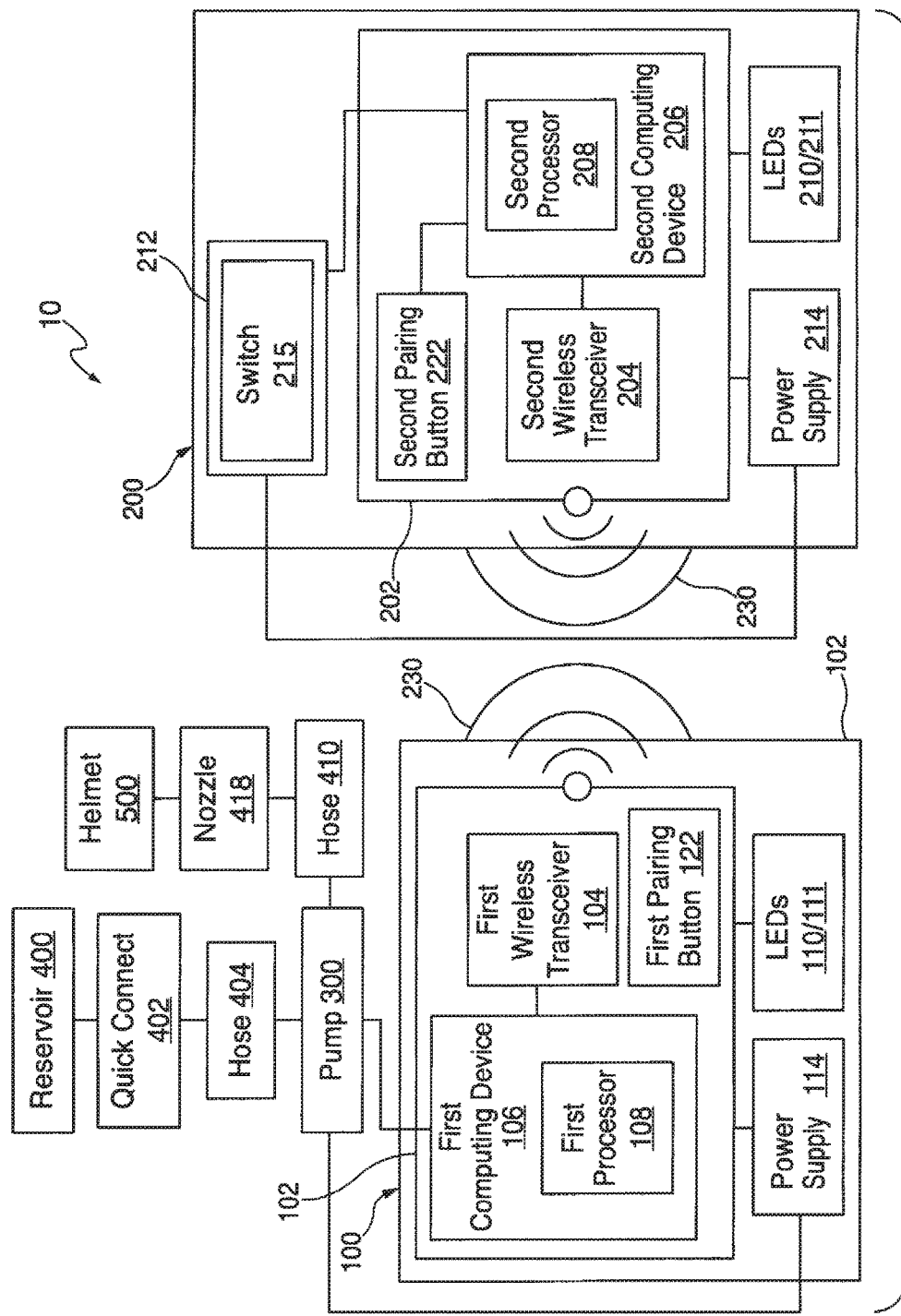
FIG. 4 shows one embodiment of a block diagram of hydration system 10.

Referring now to FIG. 4, there is shown a block diagram of one embodiment of hydration system 10. The various components of system 10 described above in connection with FIGS. 1, 2 and 3 are shown in FIG. 4. Second control system 200 communicates with first control system 100, and/or vice versa, via wireless signals 230. The user activates and/or deactivates the operation of pump 300 via user interface 212, and may pair control system 200 to control system 100 via second pairing button/device 222 of second control assembly 202. In some embodiments, both pairing buttons 122 and 222 in systems 100 and 200 are pressed to initiate, effect and complete the linking procedure.

In one embodiment, during the linking procedure a separate trigger button of second control assembly 202 is pressed to initiate selection of a random and unique communication code by processor 208, which is then transmitted to first control assembly 102 for storage in memory and subsequent retrieval therefrom for cross-checking with and confirmation of the same code subsequently received in a wireless transmission of signals from second assembly 200, more about which is said below. The generated unique communication code prevents unwanted interference or cross-talk with other nearby wireless communication devices or systems, and enhances the reliability, strength and stability of wireless communication transmission and reception between systems 100 and 200, and assemblies 102 and 202 corresponding thereto. The aforementioned trigger button may be button or switch 215, but may also be a different button (not shown in the Figures).

In one embodiment, when both control systems 100 and 200 are placed into link mode by pressing pairing buttons 122 and 222, one of the processors 108/208 in the two control assemblies is programmed to randomly select from a defined array of 5-bit addresses a unique 5-bit address. The processor also randomly selects from among a defined array of 6 wireless frequencies in the 2.4 GHz spectrum a single communication frequency to associate with the unique address that has been selected. The processor then pairs the selected unique 5-bit address with the selected wireless communication channel and stores this unique combination of a selected 5-bit address and a selected single communication frequency in memory as a unique communication code. Note that the combination of an array of 5-bit addresses and 6 randomly selectable communication frequencies yields $(6\times10)^{12}$ possible address/communication frequency combinations (6,000,000,000,000, or 6 trillion combinations). For all intents and purposes, therefore, the selected random combination or communication code is unique, and in actual practice will never be repeated or used by a different nearby wireless communication system. The second control assembly transmits that combination or code to the first control assembly when the actuator switch/button/trigger is pressed as the final step in the pairing process. The first control assembly receives and stores the combination and until relinked, will only accept instructions from a device transmitting with that exact same combination of a 5-bit address and 2.4 GHz communication frequency. In some embodiments, an opposite pairing sequence is employed, where a trigger button is located on first control assembly 102, and combination of a selected random address and a selected communication frequency is sent to second control assembly 202 from first assembly 102.

LEDs 110/111 and 210/211 may be used to visually indicate whether pairing has occurred successfully, whether power supply levels are adequate, the flow rate a user has selected, and so on.

In some embodiments, any one or more of first computing system 106 and second computing system 206 may comprise a CPU, controller, microcontroller, processor, microprocessor or any other suitable processing device 108 or 208, and may further include system memory, and a system bus that operably connects various system components, including the system memory, to processors 106 and/or 206. First or second computing devices 106 and 206 further comprise at least first and second non-transitory computer readable media configured to store first and second instructions executable by at least first processor 108 and second processor 208, respectively. Multiple processors and other multi-processor architectures also can be used to form first or second computing system 106 and/or 206. In many embodiments, a system bus is utilized, and may comprise any of several types of suitable bus architectures, including a memory bus or memory controller, a peripheral bus, or a local bus. System memory can include read only memory (ROM) and random access memory (RAM). A basic input/output system (BIOS) can be stored in ROM and contain basic routines configured to transfer information and/or data among the various elements within computing systems 106 and/or 206.

Computing systems 106 and/or 206 can include storage devices such as flash memory, RAM, ROM, and the like. Such storage devices may be configured to provide temporary or nonvolatile storage of data, data structures, and computer-executable instructions for computing systems 106 and/or 206. Any such storage media may contain computer-executable instructions for implementing one or more parts of the devices and methods described and disclosed herein.

A number of program modules may be stored in storage devices and RAM or ROM, including an operating system, one or more application programs, other program modules, and program data. The application programs and program data can include functions and methods programmed to acquire, process and display data from one or more sensors or input devices.

Figure 5:
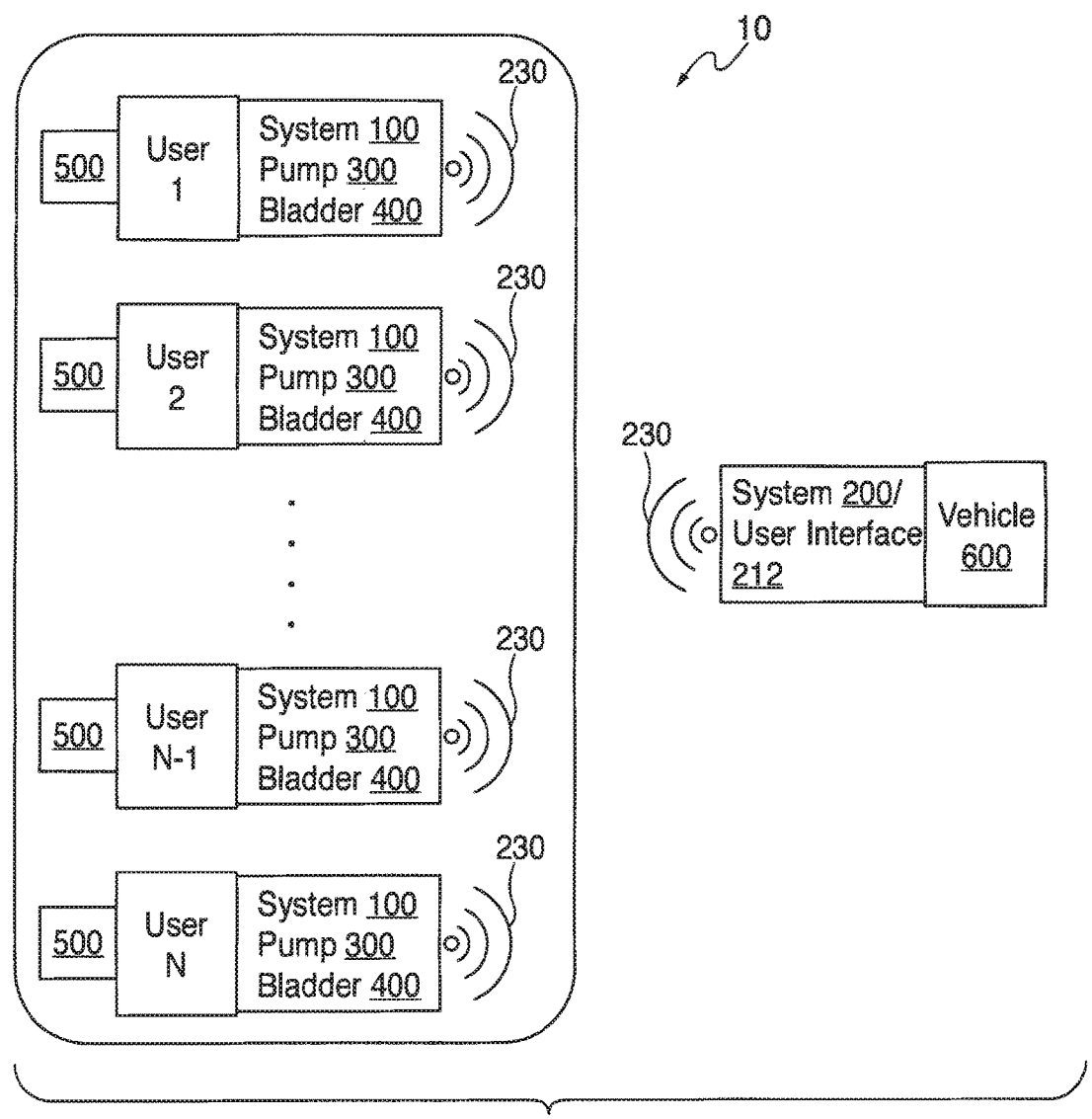
FIG. 5 shows another embodiment of a block diagram of hydration system 10 configured for multiple users of the same user interface.

FIG. 5 shows another embodiment of a block diagram of hydration system 10 configured for multiple users of the same second control system 200/user interface 212. In FIG. 5, Users 1 through N are illustrated, each having his or her own first control system 100, first control assembly 102, and associated pump 300, hydration bladder 400, and helmet 500. Each user individually wirelessly and uniquely pairs his or her own first system 100 with second system 200 (more about which is said below). Second control system 200 is mounted in or attached to vehicle 600. Processors 108 of each first control system 100 can be configured to provide random pairing of 6 channels with 5 byte addresses thereby to provide 6×10 to the 12th pairing options to second control system 200. As a result, user interface 212 of system 200 can be paired uniquely to many riders or drivers with essentially no possibility of inadvertent or unwanted crosstalk or interference from other riders using different wireless systems and communication channels. As a result, multiple riders or drivers can serially use the same user interface installed in or on a vehicle such as an automobile, motorcycle, or bicycle, while each rider or driver uses his or her own hydration backpack and systems 100, 300 and 400. Alternatively, system 10 can be configured so that fluid reservoir 400 is a large fluid container mounted in or on vehicle 600. Multiple serial users of vehicle 600 users sequentially swap out their quick-connection mechanisms 402 to fluid reservoir 400 and or/pumps 300 when they take over operation of vehicle 600. Quick-connection mechanisms to connect pump 300 to first system 100 are thus also contemplated. Further details regarding pairing are also provided below.

Figure 6:
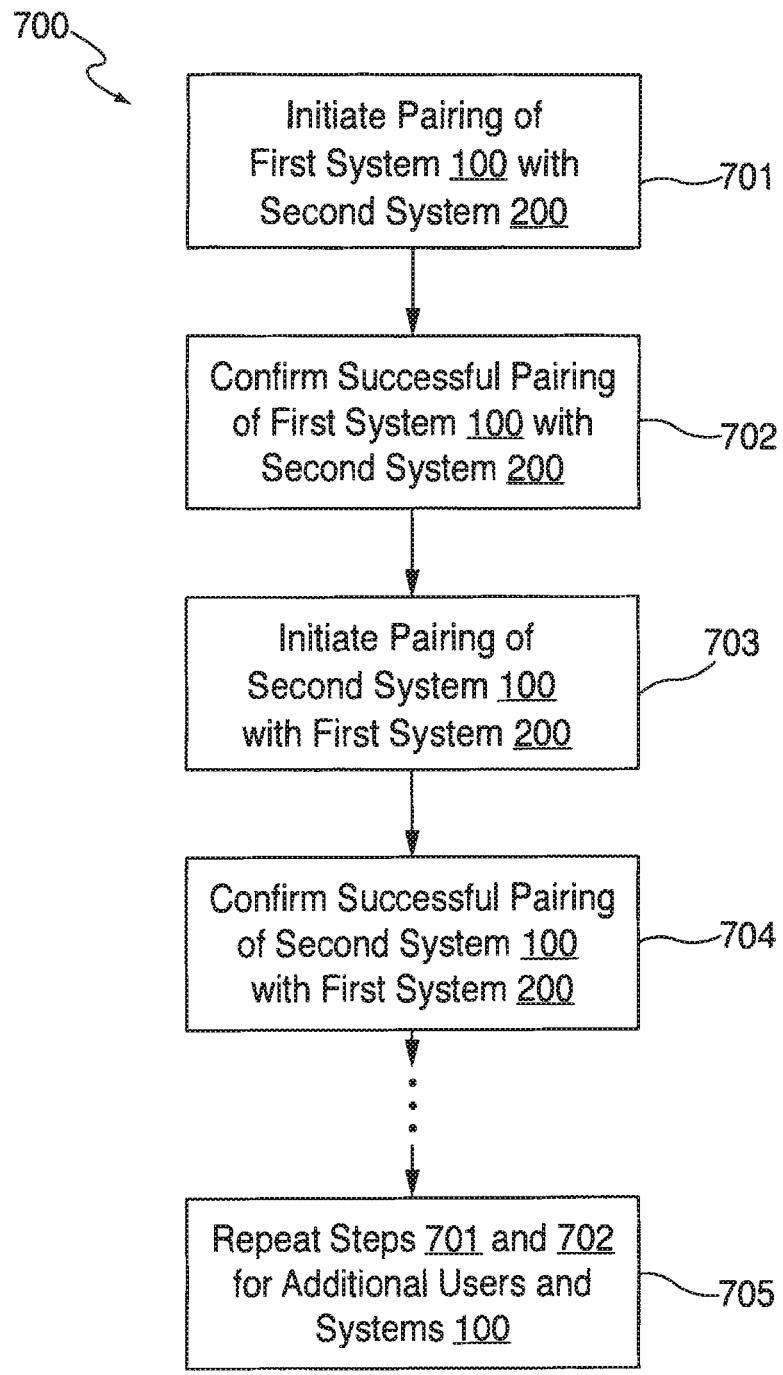
FIG. 6 shows one embodiment of a flow diagram according to one method of pairing multiple control systems 100 to a single control system 200/user interface 212.

FIG. 6 shows one embodiment of a flow diagram according to one method 700 of pairing multiple control systems 100 to a single control system 200, as described above. At Step 701, pairing of first system 100 with second system 200 is initiated. At Step 702, successful pairing of first system 100 with second system 200 is confirmed. At Step 703, pairing of second system 100 with first system 200 is initiated. At Step 704, successful pairing of second system 100 with first system 200 is confirmed. At Step 705, Steps 701 and 702, and/or Steps 703 and 704, are repeated for additional users and systems 100 and/or 200. Other combinations, permutations, and/or modifications of steps 701-705 in method 700, and of the order in which steps 701-705 are carried out, are also contemplated.

Figures 7, 7A:
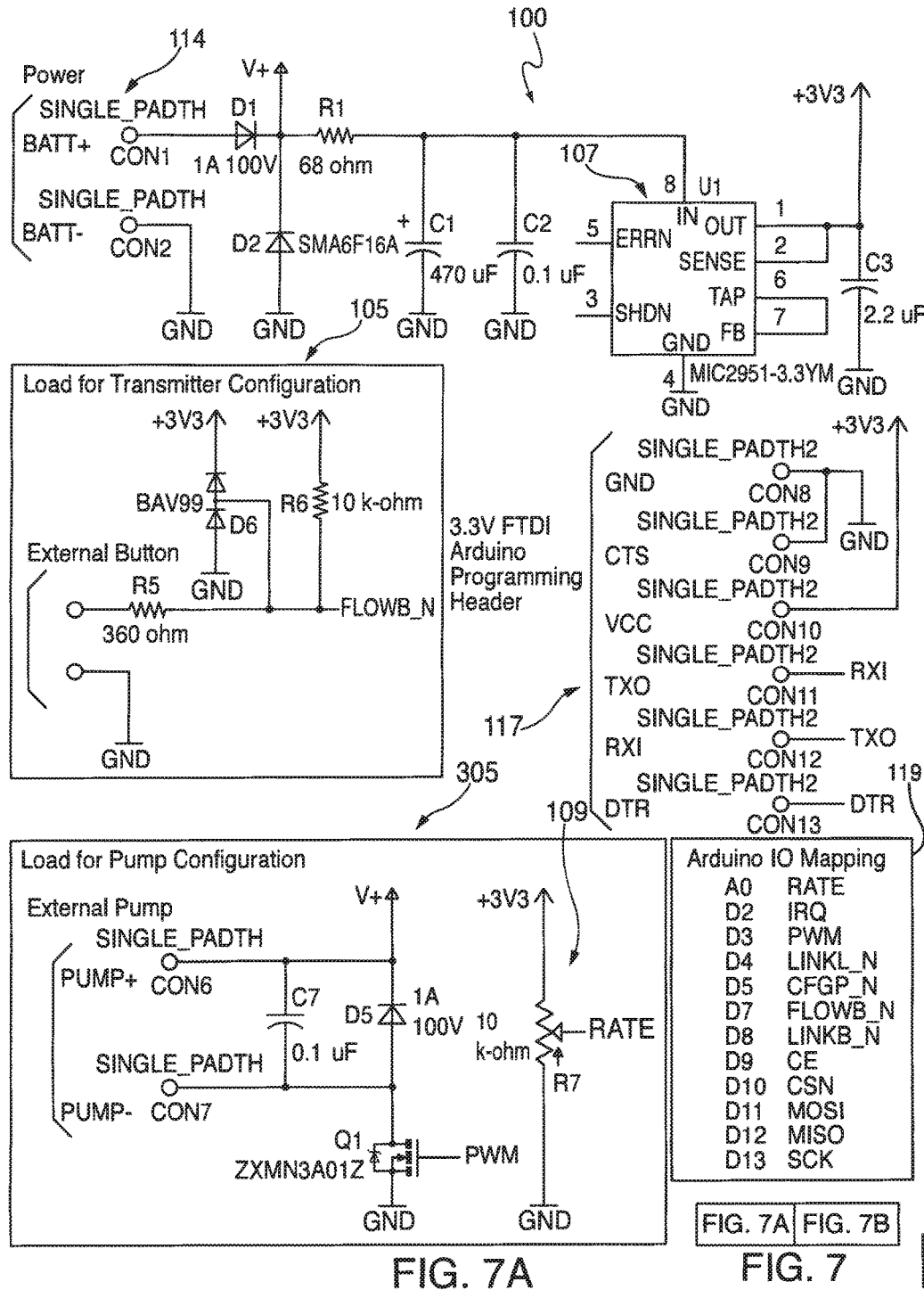
FIGS. 7(a) and 7(b) show a schematic block diagram of one embodiment of electrical and electronic circuitry associated with first control system 100.
Figure 7B:
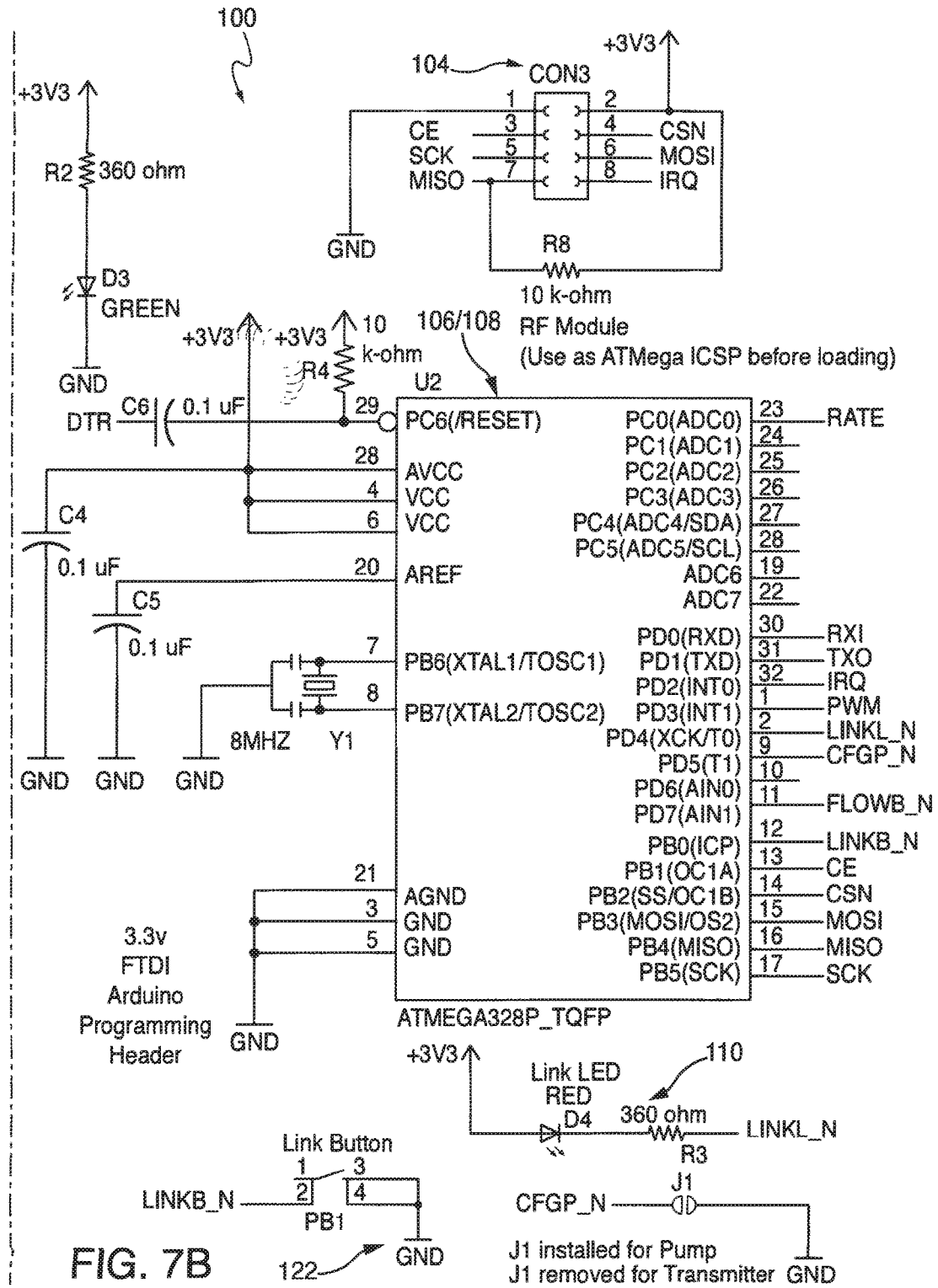

FIGS. 7(a) and 7(b) show a schematic block diagram according to one embodiment, where first computing device 106 and first processor 108 are represented by an ATMEL microprocessor programmed with an Arduino® microcontroller and associated header and interface Many other details of circuitry associated with one embodiment of first control system 100 and first control assembly 102 are shown in FIGS. 7(a) and 7(b), such as first power supply 114, first voltage regulator 107, first wireless transceiver 104, pairing button/circuit 122, potentiometer 109, load for transmitter configuration 105, load for pump configuration 305, LED 110, Arduino programming header 117, and Arduino 10 mapping 119. Those skilled in the art will understand immediately that many other substitutions, variations, modifications, and changes to the schematic block diagrams shown in FIGS. 7(a) and 7(b) may be made without departing from the spirit and scope of the various embodiments described and disclosed herein.

Continuing to refer to FIGS. 7(a) and 7(b), one example of a microprocessor suitable for use in some embodiments of first computing device 106, first processor 108, second computing device 206, and second processor 208 is the ATmega328P 8-bit AVR Microcontroller with 32K Bytes In-System Programmable Flash Processor manufactured by ATMEL® of San Jose, Calif., corresponding Datasheet Atmel-42735B-328P_Datasheet_Summary—November 2016 for which has been filed on even date herewith, and which is hereby incorporated by reference herein in its entirety. The ATmega328P microprocessor has the following features:

High-performance, Low-power AVR® 8-bit Microcontroller
Advanced RISC Architecture
  130 Powerful Instructions Most Single-clock Cycle Execution
  32×8 General Purpose Working Registers
  Fully Static Operation
  Up to 8 MIPS Throughput at 8 MHz
  On-chip 2-cycle Multiplier
Non-volatile Program and Data Memories
  32K Bytes of In-System Self-programmable Flash
  Endurance: 1,000 Write/Erase Cycles
  Optional Boot Code Section with Independent Lock Bits
  In-System Programming by On-chip Boot Program
  1K Byte EEPROM
  Endurance: 100,000 Write/Erase Cycles
  2K Bytes Internal SRAM
  Programming Lock for Software Security
JTAG (IEEE Std. 1149.1 Compliant) Interface
  Extensive On-chip Debug Support
  Programming of Flash, EEPROM, Fuses, and Lock Bits through the JTAG Interface
  Boundary-Scan Capabilities According to the JTAG Standard
Peripheral Features
  Two 8-bit Timer/Counters with Separate Prescaler and Compare Mode
  One 16-bit Timer/Counter with Separate Prescaler, Compare Mode, and
Capture Mode
  Real Time Counter with Separate Oscillator
  Four PWM Channels
  8-channel, 10-bit ADC
  Byte-oriented Two-wire Serial Interface
  Programmable Serial USART
  Master/Slave SPI Serial Interface
  Programmable Watchdog Timer with Separate On-chip Oscillator
  On-chip Analog Comparator
Special Microcontroller Features
  Power-on Reset and Programmable Brown-out Detection
  Internal Calibrated RC Oscillator
  External and Internal Interrupt Sources
  Six Sleep Modes: Idle, ADC Noise Reduction, Power-save, Power-down, Standby and Extended Standby
I/O and Packages
  32 Programmable I/O Lines
  40-pin PDIP and 44-lead TQFP
Operating Voltages
  2.7-5.5V (ATmega323L)
  4.0-5.5V (ATmega323)
Speed Grades
  0-4 MHz (ATmega323L)
  0-8 MHz (ATmega323)

Another example of a microprocessor suitable for use in some embodiments of first computing device 106, first processor 108, second computing device 206, and second processor 208 is a PIC16F1825 microprocessor manufactured by Microchip of Candler, Ariz.

Still continuing to refer to FIGS. 7(*a*) and 7(*b*), one example of a wireless transceiver suitable for use in some embodiments of wireless transceiver 104 and/or 204 is the Arduino-compatible nRF24L01+ 2.4 GHz Wireless Transceiver sold by Addicore of San Diego, Calif. and manufactured by Nordic Semiconductor of Trondheim Norway, corresponding Datasheet nRF24L01+ Single Chip 2.4 GHz Transceiver Product Specification v 1.0 for which has been filed on even date herewith, and which is hereby incorporated by reference herein in its entirety. The nRF24L01+ 2.4 GHz Wireless Transceiver has the following features:

The Addicore nRF24L01+ is a 2.4 GHz ISM band transceiver.

Includes on board support components and a 2.4 GHz antenna for easy implementation into designs without additional hardware.

Communication range 262 feet (80 meters) in ideal conditions.

A host microcontroller can communicate and configure the nRF24L01+ over a 4-pin Serial Peripheral Interface (SPI). The configuration registers are accessible through the SPI connection. Configurable parameters include frequency channel (125 selectable channels), output power, and data rate (data rates: 250 kbps, 1 Mbps, and 2 Mbps).

The on chip voltage regulator accepts supply voltages from 1.9 to 3.6V.

The module has 5V tolerant inputs which allows for direct connection of SPI pins to an Arduino microcontroller/board.

Ultra low power consumption as low as 11.3 mA transmitting, 13.5 mA receiving at 2 Mbps, 900 nA in power down, and 26uA in standby.

Internal filtering results in high margins of meeting RF regulatory standards. The module's radio uses Gaussian Frequency-Shift Keying (GFSK) modulation as well as fast Automatic Gain Control (AGC).

The module includes an Interrupt Request (IRQ) pin which can be used to wake the host microcontroller from sleep when the module receives a transmission providing great power conservation in battery devices.

Auto-acknowledge and auto-retransmit.

Continuing to refer to FIGS. 7(*a*) and 7(*b*), one example of a voltage suitable for use in some embodiments of voltage regulators 107 and/or 207 is the 150 mA Low-Dropout Voltage Regulator integrated circuit, part number MIC2951-3.3Y, manufactured by Microchip Technology of Chandler, Ariz., corresponding Datasheet M9999-021610, February, 20101, "150 mA Low-Dropout Voltage Regulator," Micrel, Inc. for which has been filed on even date herewith, and which is hereby incorporated by reference herein in its entirety. Various embodiments of the MIC2951-3.3Y integrated circuit have the following features:

High accuracy 3.3, 4.85, or 5V, 150 mA output

Low quiescent current

Low-dropout voltage

Tight load and line regulation

Very low temperature coefficient

Use as regulator or reference

Needs only 1.5 µF for stability

Current and thermal limiting

Unregulated DC input can withstand 20V reverse battery and +60V positive transients Error flag warns of output dropout (MIC2951)

Logic-controlled electronic shutdown (MIC2951)

Output programmable from 1.24V to 29V (MIC2951)

In FIGS. 7(*a*) and 7(*b*), the below descriptions and details of the various electrical and electronic components disclosed in the embodiment illustrated therein are applied thereto.

Technical Description of Schematic Block Diagram Shown in FIG. 5 Power

Batt+=power positive terminal connection
Batt−=Power negative terminal connection
D1—Diode 1 is a Schottky barrier diode which provides low on voltage and fast recovery times and low junction capacitance to provide reverse polarity protection in case the power source is connected in reverse.
D2—Diode 2 is a surface mount transient voltage suppressor that shunts to ground in cases of short high voltage pulses to protect the other circuitry. This diode starts conducting at about 17.8v and clamps (conducts all electricity) when 23.6 volts is reached.
R1—Resistor 1 is part of the circuitry to control voltages over 16v and acts as a voltage divider to reduce power dissipated in U1.
C1 and C2—Decoupling capacitors 1 and 2 when in parallel suppress high frequency noise (e.g., AC ripple) in the circuit as well as provide input stabilization for U1.
C1 and R1—Together form a low-pass filter to further reduce electrical noise from getting into and out of the digital system.
U1—MIC2951 micro power voltage regulator with a fixed 3.3v output capable of surviving surges up to 60v (e.g. vehicle load dumps). Programmable to output power from 1.24V to 29V and survive surges to 60V (load dump).
C3—Capacitor 3 is an output bypass capacitor for U1 to smooth power input to system if the voltage regulator experiences dropout.
D3—Power-on LED (green) which indicates power is supplied to system.
R2—Resistor 2 to limit the current to the LED and to prevent it from burning out from small changes in voltage.

RF Module

CON3 for nRFL2401+−2.4 GHz radio transceiver that provides transmitter and receiver capabilities to the system.

Load for Transmitter Configuration

External Button—button or user-operated input device that enables operation on demand
R5—Resistor 5 provides protection for ESD (Electrostatic Discharge) events from the button.
D6—BAV99—Dual surface mount switching diode provides protection for ESD events from the button.
R6—Resistor 6 is a pull-up resistor that keeps the FLOWB_N signal high (off) until the button is pressed. It is used instead of an internal micro-controller input for additional noise immunity.
FLOWB_N—Connection to microprocessor whereby "External Button" activation is passed into the microprocessor for processing.

Load for Pump Configuration

Pump+=positive power connection to pump
Pump−=negative power connection to pump
C7—Capacitor 7 is a bypass capacitor to filter electrical noise generated by the pump smooth power to pump in case of a transient power fluctuation or voltage drop.
D5—Schottky barrier diode provides low on voltage and fast recovery times and low junction capacitance to eliminate negative voltage spikes generated by the pump.
Q1—Enhancement mode MOSFET transistor (Trench MOSFET) provides low on-resistance and fast switching speed to switch power on and off to the pump.
R7—Potentiometer used to define flow duration from button press. At lowest setting the pump operates in "momentary mode" and pump stays on as long as "External Button" is pressed or engaged. As the potentiometer is turned clockwise past the half-way point, the pump duration increases, for example to 1 second, 2 seconds, 3 seconds, 4 seconds, and/or 5 seconds. This means that if the potentiometer is set at value "3", when the user presses the button or engages the "External Button" for any time at all, that the pump will operate for 3 seconds only and then turns off and waits for a new button press.
RATE—Rate is the input to the microprocessor of the potentiometer value selected by the user.

3.3v FTDI Arduino Programming Header

Programming header interface on the PCB.
Also used to diagnose operational issues and performance.

Link Button

PB1—Onboard push button that is used to place module into Link Mode.
LINKB_N—connection to the microprocessor at pin 12
Link LED
D4—LED (red) lights up when the module enters "link mode" by pressing the "PB1 Link Button". The red LDE turns off if pairing is successful. This LED provides diagnostics regarding whether or not linking to another module has been successful. This LED also provides diagnostics regarding whether or not a linked connection has been lost. Diagnostics are revealed via a defined blink sequence for either linking issue.
R3—Resistor 3 to limit the current to the LED and to prevent it from burning out from small changes in voltage.
LINKL_N—input to D4 from microprocessor to power on and power off the D4 LED. Potentiometer
J1—an optional solder-jumper that can be used to inform the firmware running on the micro-controller that the device is configured as a transmitter or receiver.

The "Load for Pump Configuration" and "Load for Transmitter Configuration" sections identify the position-specific set of components to be loaded if separate printed circuit boards are built for each function (e.g., to reduce cost). The schematic of FIG. 5 indicates what would need to be installed and/or removed for differentiation of systems 100 and 2000.

Microprocessor

U2—ATMega328P_TQFP
The remaining components do the following:
C6—provides an AC couple from a signal on the programming header to reset the micro-controller at the start of a programming operation.
R4—a pull-up resistor on the micro-controller reset line.
C4—bypass capacitors for the micro-controller voltage supply.
C5—filter capacitor for the micro-controller internal ADC (analog-to-digital converter) voltage reference (used to measure the potentiometer voltage).
Y1—8 MHz resonator to provide the clock signal for the micro-controller.

R8—pull-up resistor on the data line from the NRF24L01 module to the micro-controller.

Further to the schematic block diagram shown in FIGS. 7(*a*) and 7(*b*), and according to one embodiment, provided below in Table 1 are examples of pseudo-code software modules that may be loaded into the memory of, and executable by, first processor 108 and/or second processor 208.

Table 1: Pseudo-Code Example Software Modules for Processors 108 and 208

```
//
=========================================================================
===
// Timer Module
//
// Provides timing control for evaluation of periodic tasks.
Implemented
// using a callback executed every 10 mSec.  Output are two variables
that
// are designed to be consumed in the main execution loop. fastTick
is true
// once every 10 mSec.  slowTick is true once every second.
//

//
// Activity Timer Configuration
//
#define TIMER_MSEC       10
#define TIMER_SEC_COUNT (1000/TIMER_MSEC)

void InitTimer()
{
  Timer1.initialize();
  Timer1.attachInterrupt(ActivityTimerTask, 1000*TIMER_MSEC);
  isrTimerTick = false;
  fastTick = false;
  slowTick = false;
  timerSecCount = TIMER_SEC_COUNT;
} void EvalTimer()
{
  // Tick values will be set as necessary
  fastTick = false;
  slowTick = false;
```

```
  if (isrTimerTick) {
    isrTimerTick = false;
    fastTick = true;
    if (--timerSecCount == 0) {
      slowTick = true;
      timerSecCount = TIMER_SEC_COUNT;
    }
  }
}

//
//=======================================================================
// Button Module
//
// Senses, debounces and implements related functionality from the button
// inputs.  Link Button functionality includes toggling the device mode
// between normal operation and link mode.  Flow Button functionality is
// dependent on mode.  In normal operation mode, flow button presses
// initiate transmission of enable flow packets and flow button releases
// initiate transmission of disable flow packets.  In link mode, short
// button presses initiate a link process using new link parameters and
// long (more than 2 second) presses initiate a link process using existing
// link parameters.
//

//
// Long-press period in msec (should be a multiple of TIMER_MSEC)
//
define BUTTON_LONG_PRESS_MSEC 2000 void InitButtons()
{
```

```
  buttonDown[LINK_BUTTON_I] = false;
  buttonDown[FLOW_BUTTON_I] = false;
  buttonPrev[LINK_BUTTON_I] = false;
  buttonPrev[FLOW_BUTTON_I] = false;
  buttonPressDetected[LINK_BUTTON_I] = false;
  buttonPressDetected[FLOW_BUTTON_I] = false;
  buttonReleaseDetected[LINK_BUTTON_I] = false;
  buttonReleaseDetected[FLOW_BUTTON_I] = false;
  buttonDebounceCount[LINK_BUTTON_I] =
LINK_BUTTON_DBNC_MSEC/TIMER_MSEC;
  buttonDebounceCount[FLOW_BUTTON_I] =
LINK_BUTTON_DBNC_MSEC/TIMER_MSEC;
  buttonPressTimer[LINK_BUTTON_I] =
BUTTON_LONG_PRESS_MSEC/TIMER_MSEC;
  buttonPressTimer[FLOW_BUTTON_I] =
BUTTON_LONG_PRESS_MSEC/TIMER_MSEC;
} void EvalButtons()
{
  // Link Button
  _EvalOneButton(LINK_BUTTON_I);
  if (LINK_BUTTON_PRESSED()) {
    // Toggle Link Mode
    CmdSetLinkMode(!(CmdIsInLinkMode()));
  }

// Flow Button
  _EvalOneButton(FLOW_BUTTON_I);
  if (CmdIsInLinkMode()) {
    if (FLOW_BUTTON_RELEASED()) {
      CmdLinkDevices(FLOW_BUTTON_LONGPRESS());
    }
  } else {
    if (FLOW_BUTTON_PRESSED()) {
      CmdSetFlowMode(true);
    }
    if (FLOW_BUTTON_RELEASED()) {
      CmdSetFlowMode(false);
    }
  }
```

```
  // Note activity
  if (LINK_BUTTON_PRESSED() || FLOW_BUTTON_PRESSED()) {
    PowerActivity();
  }
}

//
=======================================================================
===
// Command Module
//
// Implements the main logic functionality of the program.
//    1. Process received packets from another device.
//       a. Flow control enable and disable packets to inform
//          the pump control logic of user actions.
//       b. Set Link parameters packets are stored and state
//          set to update local link state upon receipt of
//          Exit Link mode packet.
//       c. Exit Link mode packet initiates storing received
//          link parameters and exit link mode.
//    2. Continuously transmit flow enable messages after noting
//       flow button was pressed at a period rate (30 msec) to
//       so that remote pump runs continuously while button is
//       pressed even if there is unreliable radio communication
//       between devices.
//    3. Handle link mode logic including initiating link sequence
//       with either new or existing link parameters when commanded
//       by a pump button press while in link mode.  Send the
parameters
//       in one packet that must be acknowledged by the receiver and
//       after acknowledgement take both devices out of link mode,
storing
//       any new parameters locally as well.  Indicate an error if the
//       remote device did not acknowledge.
//    4. Time link mode out back into normal operation if there is no
//       user activity in one minute.
//    5. Note user activity to the power management module to prevent
//       device from going into low power mode prematurely.

//
```

```
//  Send frequency for pump on (should be less than PUMP_ON_MSEC and a
multiple of TIMER_MSEC)
//
#define CMD_PUMP_RESEND_MSEC 30

//
// Link Mode timeout (multiple of TIMER_MSEC, less than
65535*TIMER_MSEC)
//
define CMD_LINK_TO_MSEC     60000 void InitCmd()
{
  cmdFlowInProgress = false;
  cmdLinkMode = false;
  cmdLinkState = LINK_ST_IDLE;
} void EvalCmd()
{
  // Evaluate the flow timer if it is running
  if (cmdFlowInProgress) {
    if (--cmdFlowTimeoutCount == 0) {
      // Send another pump enable packet
      cmdFlowTimeoutCount = CMD_PUMP_RESEND_MSEC/TIMER_MSEC;
      _cmdSendFlowPacket(true);
      EnablePump(true);
    }
  }

// Evaluate the link timeout timer if it is running
  if (cmdLinkMode) {
    if (--cmdLinkTimeoutCount == 0) {
      CmdSetLinkMode(false);
    }
  }
} boolean CmdIsInLinkMode()
{
```

```c
    return(cmdLinkMode);
} void CmdProcessRxPkt(uint8_t* pktP, uint8_t pktLen)
{
  // Process command
  switch (*pktP) {
    case CMD_FLOW_CONTROL:
      if ((pktLen == CMD_PKT_LEN) && !cmdLinkMode) {
        if (*++pktP == 0) {
          EnablePump(false);
        } else {
          EnablePump(true);
        }
      }
      break;

case CMD_SET_RF_CFG:
      if ((pktLen == CMD_PKT_LEN) && (cmdLinkState == LINK_ST_CFG)) {
        // Unpack and save the link arguments
        cmdLinkCh = *++pktP;
        cmdLinkAddr[4] = *++pktP;
        cmdLinkAddr[3] = *++pktP;
        cmdLinkAddr[2] = *++pktP;
        cmdLinkAddr[1] = *++pktP;
        cmdLinkAddr[0] = *++pktP;
        cmdLinkState = LINK_ST_EXIT;
      }
      break;

case CMD_EXIT_CFG:
      if ((pktLen == CMD_PKT_LEN) && (cmdLinkState == LINK_ST_EXIT))
{
        _cmdSaveLinkInformation(cmdLinkCh, cmdLinkAddr);
        CmdSetLinkMode(false);
      }
      break;
  }

// Note activity
  PowerActivity();
}
```

```
void CmdSetLinkMode(boolean en)
{
  if (en) {
    // Configure link mode
    if (cmdFlowInProgress) {
      // Stop any ongoing flow
      CmdSetFlowMode(false);
    }
    cmdLinkMode = true;
    cmdLinkState = LINK_ST_CFG;
    SetLedLink();
    cmdLinkTimeoutCount = CMD_LINK_TO_MSEC/TIMER_MSEC;
  } else {
    // Disable link mode
    cmdLinkMode = false;
    cmdLinkState = LINK_ST_IDLE;
    SetLedIdle();
  }
  InitRadio(false, cmdLinkMode);
} void CmdSetFlowMode(boolean en)
{
  if (en) {
    // Start flow
    cmdFlowInProgress = true;
    cmdFlowTimeoutCount = CMD_PUMP_RESEND_MSEC/TIMER_MSEC;
    _cmdSendFlowPacket(true);
    EnablePump(true);
  } else {
    // End flow
    if (cmdFlowInProgress) {
      cmdFlowInProgress = false;
      _cmdSendFlowPacket(false);
      EnablePump(false);
    }
  }
}
```

```
void CmdLinkDevices(boolean reuseLinkInfo)
{
  uint8_t linkCh;
  uint8_t linkAddr[5];

// Get a new link configuration if requested to, otherwise use
existing configuration
  if (reuseLinkInfo) {
    PS_GetAddr(1, linkAddr);
    linkCh = PS_GetChannel(1);
  } else {
    LinkComputeInfo(&linkCh, linkAddr);
  }
  LinkLogInfo(linkCh, linkAddr);

// Try to send the new link configuration to the other device and,
if successful, save it for ourselves
  if (_cmdSendLinkPacket(linkCh, linkAddr)) {
    // Receiver successfully got packet so we see if we can take them
out of Link Mode
    if (_cmdSendLinkExitPacket()) {
      _cmdSaveLinkInformation(linkCh, linkAddr);
    } else {
      // Indicate failure
      SetLedError(LED_ERR_LINK);
    }
  } else {
    // Indicate failure
    SetLedError(LED_ERR_LINK);
  }
  CmdSetLinkMode(false);
}

//
=========================================================================
===
// LED Indicator Module
//
// Control the indicator LED.
//   1. Indicate entry to and exit from link mode (LED lit while in
link mode)
```

```
//   2. Manage timing to blink LED for error conditions.  LED blinks a number of
//      times associated with an error and then is dark between blink series as
//      a demarcation.
//      a. Blink twice for radio-related errors (radio not attached, cannot be configured)
//      b. Blink three times for missed packets during link operation
//      c. Blink four times for missed packets during normal operation
//

//
// LED State
//
#define LED_ST_IDLE           0
#define LED_ST_LINK           1
#define LED_ST_ERR_BLINK_ON   2
#define LED_ST_ERR_BLINK_OFF  3
#define LED_ST_ERR_BLINK_WAIT 4

//
// Error Blink Counts
//
#define LED_ERR_NRF_COUNT   2
#define LED_ERR_LINK_COUNT  3
#define LED_ERR_CONN_COUNT  4

//
// Error timing (mSec - must be a multiple of TIMER_MSEC)
//
#define LED_ERR_BLINK_TIME   200
define LED_ERR_OFF_TIME     750 void InitLED()
{
  // IO
  _SetLed(false);

// State
  ledState = LED_ST_IDLE;
```

```
    ledCurErr = LED_ERR_NONE;
} void EvalLED()
{
  // Evaluate blinking error code if running
  if (ledCurErr != LED_ERR_NONE) {
    if (--ledErrTimer == 0) {
      switch (ledState) {
        case LED_ST_ERR_BLINK_ON:  // "ON" during a blink sequence
          _SetLed(false);
          if (--ledErrCounter == 0) {
            // Done with this blink sequence
            ledErrCounter = ledErrCount;   // Reset for next sequence
            ledState = LED_ST_ERR_BLINK_WAIT;
            ledErrTimer = LED_ERR_OFF_TIME/TIMER_MSEC;
          } else {
            // Still in blink sequence
            ledState = LED_ST_ERR_BLINK_OFF;
            ledErrTimer = LED_ERR_BLINK_TIME/TIMER_MSEC;
          }
          break;

case LED_ST_ERR_BLINK_OFF:  // "OFF" during a blink sequence
          _SetLed(true);
          ledState = LED_ST_ERR_BLINK_ON;
          ledErrTimer = LED_ERR_BLINK_TIME/TIMER_MSEC;
          break;

case LED_ST_ERR_BLINK_WAIT:  // Waiting between blink sequences
          _SetLed(true);
          ledState = LED_ST_ERR_BLINK_ON;
          ledErrTimer = LED_ERR_BLINK_TIME/TIMER_MSEC;
          break;

default:
          // Set sane state
          if (CmdIsInLinkMode()) {
            SetLedLink();
          } else {
          SetLedIdle();
```

```
          }
        }
      }
    }
} void SetLedIdle()
{
  _SetLed(false);
  ledState = LED_ST_IDLE;
  ledCurErr = LED_ERR_NONE;
} void SetLedLink()
{
  _SetLed(true);
  ledState = LED_ST_LINK;
  ledCurErr = LED_ERR_NONE;
} void SetLedError(uint8_t errT)
{
  if (errT != ledCurErr) {
    // Assume valid error
    ledState = LED_ST_ERR_BLINK_ON;
    ledErrTimer = LED_ERR_BLINK_TIME/TIMER_MSEC;
    ledCurErr = errT;
    _SetLed(true);

switch (errT) {
      case LED_ERR_NRF:
        ledErrCount = LED_ERR_NRF_COUNT;
        break;

case LED_ERR_LINK:
        ledErrCount = LED_ERR_LINK_COUNT;
        break;

case LED_ERR_CONN:
        ledErrCount = LED_ERR_CONN_COUNT;
```

```
        break;

default:
        SetLedIdle();
    }
    ledErrCounter = ledErrCount;
  }
}

//
//=======================================================================
===
// Device Link Module
//
// Compute link parameters including radio channel selected to avoid most
// 802.11b WiFi channels and radio packet custom address bytes.  Five address
// bytes are used by the radio to differentiate packets so that many pairs
// of devices can co-exist.  Address bytes are selected randomly with slight
// modification of one byte to prevent confusion by the radio's discriminator.
//

//
// Legal Channels - selected to exist between primary WiFi channels 3 and 11 (to
// avoid the main power carrying frequencies of both 802.11g and 801.11n)
//
#define NUM_LEGAL_CHANNELS 6
const uint8_t legalChannels[NUM_LEGAL_CHANNELS] PROGMEM = {2, 4, 40, 42, 44, 78};

#define NUM_LEGAL_ADDR_BYTES 40
const uint8_t legalAddrBytes[NUM_LEGAL_ADDR_BYTES] PROGMEM = {
  0xF0, 0xF2, 0xF4, 0xF6, 0x0F, 0x2F, 0x4F, 0x6F,
  0xE0, 0xE2, 0xE4, 0xE6, 0x0E, 0x2E, 0x4E, 0x6E,
```

```
  0x30, 0x32, 0x34, 0x36, 0x03, 0x23, 0x43, 0x63,
  0x10, 0x12, 0x14, 0x16, 0x01, 0x21, 0x41, 0x61,
  0xEE, 0x33, 0x11, 0x55, 0x77, 0xCC, 0x88, 0xAA
};

void LinkComputeInfo(uint8_t* chP, uint8_t* aP)
{
  long r;
  uint8_t i;

// Initialize our random number generator with as much randomness as we can
  r = millis() * GetPumpPot();
  randomSeed(r);

// Select a Channel randomly from our legal set
  r = random(0, NUM_LEGAL_CHANNELS);
  *chP = pgm_read_byte(&legalChannels[r]);

// Select a legal address randomly
  for (i=0; i<5; i++) {
    *(aP + i) = _linkGetRandomAddrByte(i==4);
  }
}

// We cannot allow the first byte in the address field (the MSbyte to equal 0x00, 0xFF,
// 0xAA or 0x55 per the Nordic spec because that can cause it to misinterpret and miss
// the packet.
uint8_t _linkGetRandomAddrByte(boolean isMSbyte)
{
  uint8_t r;

r = random(0, 255);

if (isMSbyte) {
    while ((r == 0x00) || (r == 0xFF) || (r == 0xAA) || (r == 0x55))
    {
      r = random(0, 255);
    }
  }
```

```
    return(r);
} uint8_t _linkGetRandomAddrByteFromList(boolean isMSbyte)
{
  uint8_t i;
  uint8_t r;

i = random(0, NUM_LEGAL_ADDR_BYTES);
  r = pgm_read_byte(&legalAddrBytes[i]);

if (isMSbyte) {
    while ((r == 0x00) || (r == 0xFF) || (r == 0xAA) || (r == 0x55))
{
      i = random(0, NUM_LEGAL_ADDR_BYTES);
      r = pgm_read_byte(&legalAddrBytes[i]);
    }
  } return(r);
}

//
//=========================================================================
===
// Power Management Module
//
// Provides a timer that, when expired, will put the processor and attached
// radio into a low power mode to save external battery power.  Low-power
// mode may be exited when the pump button is pressed.  The timer is reset
// whenever code calls the PowerActivity subroutine.
//

//
// Power-down time (seconds)
//
#define POWER_DOWN_TIME 3600
```

```
void InitPower()
{
  // Initialize our timer
  PowerActivity();
}

// Called as a periodic activity (every TIMER_MSEC msec)
void EvalPower()
{
  if (--powerTimer == 0) {
    // Setup sleep
    _powerGotoSleep();  // Returns when we wake up // Resume normal operation after restoring some system state
    _powerWake();
  }
} void PowerActivity()
{
  powerTimer = POWER_DOWN_TIME * TIMER_SEC_COUNT;
}

//
//==========================================================================
//
// Pump Control Module
//
// Controls operation of the pump in two modes selected by an external analog
// signal (connected to a potentiometer).
//   1. Normal Pump Operation - selected when the 10-bit ADC reading the pot
//      returns is less than 512 (half-way point).  The pump essentially
//      follows the remote pump enable button.  A timer with a period longer
//      than the repeated pump enable packets keeps the pump running in the case
```

```
//      a few packets are lost in transmission.  The period is short enough so
//      that humans perceive the pump as stopping when the button is released
//      (case that packets stop altogether).  The pump disable packet also
//      immediately stops the pump.
//  2. Burst Pump Operation - selected when the 10-bit ADC reading the pot
//      returns is greater than 512.  A burst period is computed between 2
//      and 5 seconds based on the ADC value between 512 and 1023 (the upper
//      half of the potentiometers rotation).  A pump enable packet initiates
//      a continuous operation of the pump for this burst period. Pump disable
//      packets are ignored.
//

//
// Pump on minimum interval (mSec - must be a multiple of TIMER_MSEC)
//
#define PUMP_ON_MSEC   280

//
// Pump burst range (mSec - must be a multiple of TIMER_MSEC)
//
#define PUMP_BURST_MIN 2000
define PUMP_BURST_MAX 5000 void InitPump()
{
  // IO
  pinMode(POT_IN, INPUT);
  pinMode(PUMP_OUT, OUTPUT);
  _SetPump(false);

// State
  pumpDurationAdc = 9999;  // force the first call to GetPumpDuration
  pumpOnTimer = 0;

// Get initial duration
```

```
  GetPumpDuration();
} void EvalPump()
{
  uint16_t a;

// Evaluate the pump timer if it is running
  if (pumpOnTimer != 0) {
    if (--pumpOnTimer == 0) {
      _SetPump(false);
    }
  }

// Evaluate pump duration input
  GetPumpDuration();
} void EnablePump(boolean en)
{
  if (pumpBurstMode) {
    // Burst mode: trigger pump only if it is not currently running
    if (en && !pumpRunning) {
      _SetPump(true);
      pumpOnTimer = pumpDurationTime;
    }
  } else {
    // Normal operation, pump follows button with minimum on-time
    if (en) {
      // Start or continue pump
      _SetPump(true);
      pumpOnTimer = pumpDurationTime;
    } else {
      // Stop pump
      _SetPump(false);
      pumpOnTimer = 0;
    }
  }
}
```

```
void GetPumpDuration()
{
  int newVal;

newVal = GetPumpPot();

// Provide some hysteresis to prevent jumping back and forth
between normal and burst mode
  if (abs(newVal - pumpDurationAdc) > 5) {
    pumpDurationAdc = newVal;
    if (pumpDurationAdc < 512) {
      pumpBurstMode = false;
      pumpDurationTime = PUMP_ON_MSEC/TIMER_MSEC;
    } else {
      pumpBurstMode = true;
      pumpDurationTime = map(pumpDurationAdc, 512, 1023,
PUMP_BURST_MIN/TIMER_MSEC, PUMP_BURST_MAX/TIMER_MSEC);
    }

// Note activity
    PowerActivity();
  }
}

//
=========================================================================
===
// Main Loop
//
// Evaluate the various program modules in order.  Real-time
activities including
// the timer and radio are evaluated constantly.  Periodic activities
are evaluated
// once every 10 mSec.
//
void main(void) {
  InitSystem();

while (1) {
    EvalTimer();
    EvalRadio();
```

```
    // Periodic Activities
    if (fastTick) {
      EvalButtons();
      EvalCmd();
      EvalLED();
      EvalPower();
      EvalPump();
    }
  }
}

// PWM Pump Control
// Pump Fade

// Increase and decrease the intensity/speed at which a pump operates

*/
int motor = 9;     //Must be PWM pin, goes to motor (gate)
int intensity = 0; //Actual tension: 12 -(255-intensity)*5/255
int crease = 3;   //Changes motor intensity
void setup()  {
  pinMode(motor, OUTPUT);
}
void loop()  {
  analogWrite(motor, intensity);  //Writes PWM to the motor
  intensity = intensity + crease;
  if (intensity == 0 || intensity == 255) {
    crease = -crease ;  //Increase to decrease due to line 21
  }
  delay(3000); //Making this too small can damage the motor
}
```

According to some embodiments, provided below are further descriptions of how LEDs and pairing can be configured and executed in systems 100 and 200. Note that in one embodiment a lit green LED indicates that power is on. The green LED should be on when assembly 102 or 202 has electrical power provided thereto. Also pairing button 122 and/or 222 should be pressed to set a device to Link Mode (pairing mode). The pairing button should be pressed again to resume normal operation and not to pair or to unpair.

Link Procedures
1. Press pairing button on both devices to initiate the linking process. Red LED turns on indicating Link Mode.
2. Press and release switch or button 215 of user interface 212 of the second control system 200 (the transmitter). This finalizes the linking process
3. Red LEDs should be turned off on both systems 100 and 20 indicating successful pairing. Now each system has a custom RF Channel/Address combination.
4. If the Red LED on the transmitter blinks a pattern and the Red LED on the receiver shines steady and does not go out then the link failed. Try again.
5. The transmitter will not change its configuration unless it gets an acknowledgement that the receiver also successfully received the link information.
   Link second, third or more pump modules associated with the first control assembly 102 to the same user interface button of a second control assembly 202:
   A. Press link button on transmitter and new receiver (pump).
   B. Red LED is lit.
   C. Press and hold down button for more than 2 seconds (perhaps say 3 seconds) and release.
   D. Both LEDs should go out.
   E. Now when the transmitter pump button is pushed then both pumps should run.

Red LED has multi-use functionality
1. Solid red LED on indicates Link Mode
2. Repeating 2 blinks followed by a short pause indicates that the microcontroller could not successfully communicate with its own radio module.
2. Repeating 3 blinks followed by a short pause indicates that the transmitter could not verify the receiver was properly linked.
3. Repeating 4 blinks followed by a short pause indicates that the transmitter was unsuccessful in sending a pump command to the receiver. This usually occurs when the receiver is turned off or not properly linked, and can also happen if there is too much distance or interference between the transmitter and receiver.

LED and repeating packets
1. While the pump button is pressed, the transmitter sends a "Pump On" packet every 50 mSec. The receiver starts the pump for a 200 msec period. This way it can miss an occasional "Pump On" packet while the button is pressed.
2. When the pump button is released, the transmitter sends a "Pump Off" packet and the receiver immediately shuts the pump off.
3. The 200 msec window ensures the pump will turn off quickly even if the "Pump Off" packet is lost.
4. The transmitter actually will attempt to send each packet up to 6 times before giving up for that packet and starting the 4 blink indication.
5. The next successfully transmitted packets stops the LED from blinking.

Burst duration
1. The Potentiometer provides different pump durations from a single button press and is adjustable in the second control assembly.

Sleep Mode
1. The modules while in normal operation mode take between 20-30 mA while idling.
2. In sleep mode, current draw is reduced.
3. The transmitter module is awakened by a button press.
4. The transmitter wakes the pump module.
5. Either module can be woken by recycling power.

Diagnostic Code
1. There is a diagnostic function included in the code that outputs various diagnostic messages to the serial port on an Arduino board/microcontroller.
2. If a computer is attached via the FTDI interface, the diagnostic messages can be viewed.
3. Messages may be used to diagnose manufacturing problems, faulty units, and/or damaged units.

In some embodiments, first and second control assemblies 102 and 202 are housed in water resistant or waterproof enclosures 103 and 203, and wireless transceivers 104 and 204 operate at 2.4 GHz. Other wireless frequencies are of course contemplated. As described above, processors 108 and 208 can be configured to provide random pairing of 6 channels with 5 byte addresses thereby to provide 6×10 to the 12th pairing options. As a result, one button (on a bike or car, for example) can be paired uniquely to many riders or drivers with essentially no possibility of inadvertent or unwanted crosstalk or interference from other riders using different wireless systems and communication channels.

In the various embodiments, pump 300 of system 10 can be configured to be software driven as opposed to relay-driven; advantageously, no power relay is required to drive and control pump 300, which can be driven and controlled directly under software control by first control assembly 102, first computing system 106, and first processor 108. In some embodiments, bi-directional communication between transmitters and receivers is enabled, which permits real-time operational status to be provided, such as whether or not systems 100 and 200 have been paired, signal(s) have been transmitted and/or received successfully, signal(s) have been lost, no receiver is in range, battery power status, whether software has assigned a module a role (e.g., 'transmitter' role assigned to module if a button or other device is connected to the transmitter position on printed circuit board (PCB) 120 or 220; 'receiver' role assigned to the module if a pump or other device is connected to the receiver position on the PCB). Software can be configured to dictate the function of a module or system based on connections to the PCB in the transmitter and/or receiver positions. Software can also be configured to assign a 'transmitter' and/or 'receiver' role to a single module if a button/device is connected to transmitter position on the PCB and if a pump/device is connected to the receiver position on the same PCB.

In addition, modules or systems 100 and 200 may be paired to one or more modules or systems to provide:

User initiated pairing of one transmitter to one receiver

User initiated pairing of one transmitter to many receivers

User initiated pairing of many transmitters to one receiver

User-selectable pump operation modes are also possible, such as

Momentary 3 second burst 5 second burst user-defined burst length

Note that in some embodiments of system 10 "transmitters" and "receivers" are interchangeable in systems 100 and 200 seeing as in some embodiments wireless transceivers 104 and 204 may be employed in both of systems 100 and 200, which adds considerably to the flexibility and range of configurability of hydration system 10. In other embodiments, a transmitter chip is used in one of systems 100 and 200, and a receiver chip is used in the other of systems 100 and 200.

Power management of system 10 can be configured to provide any one or more of the following:

Automatic power into low power mode after period of no use

Automatic power off after longer period of no use

User-initiated wake-up from low power and power-off mode

In terms of signal redundancy, transmission and reception, the following provisions can be made:

Transmission of repeating "pump-on" packets for duration of button press or for duration of user-selected operation mode.

Transmission of pump-off command when button press is over or at end of user-selected operation mode.

Receiver enters listening mode after reception of first pump-on packet. Note that once powered on systems 100 and 200 are both always in listening mode unless they are transmitting, and remain so until powered off.

Receiver initiated repeating listening commands until pump-off command is received or missed packet threshold is reached.

Receiver ends pump operation when pump-off command is received.

Receiver ends pump operation if a threshold of missed pump-on packets is reached to avoid flooding user.

User-initiated pairing of 2.4 Ghz random channels/frequencies and pipe addresses from a matrix of legal channels and addresses.

Over 1 trillion pairing options eliminates cross-talk and interference.

User-selectable stream/flow control via SW enabled/controlled pulsed-width modulation of the signal to the pump from the receiver User can set stream/flow control via the push button/transmitter Transmitter sends user input for flow control to the receiver Receiver accepts input from the transmitter and enters new operational mode for flow based on the input from the transmitter/button assembly.

With respect to printed circuit boards 120 and 220, the following provisions, adaptations or modifications may also be made:

Identical control assemblies for transmitter (Tx) and receiver (Rx).

Software (SW) defined role (Tx, Rx) based on device connections to PCB.

On board potentiometer for hardware controlled flow rate.

Reprogrammable microprocessor to provide upgrade capabilities.

Onboard automotive grade voltage regulator to provide for operation of either module in voltages ranging from 6 v to 24 v DC.

Electronic circuit and components provide voltage spike and surge suppression, electro-magnetic interference (EMI) suppression, reverse polarity protection.

System 10 may further be configured to include one or more optical switches, fingerprint readers, or proximity sensors. System 10 can be configured to provide relatively effortless hydration at any speed in any terrain. Constant hydration bursts can relieve user tension and heighten or improve user focus. Regular hydration bursts provided to a user are more beneficial than periodic gulps of liquid in larger amounts.

In some embodiments, a relay may be connected to pump 300 and be driven by first control assembly 102 such that larger electrical currents may be employed, and larger devices can be controlled remotely, using system 10.

Additionally, note that system 10 is not intended to be limited to embodiments employing the specific Arduino-compatible processors and devices, the specific circuits and schematics, or the specific programming code disclosed and described herein. Instead, and as those skilled in the art will appreciate immediately after having read and understood the specification, drawings and claims hereof, many other types of processors, circuits, programs and programming code other than those disclosed explicitly herein may be employed without departing from the spirit and scope of the various inventions disclosed and described herein.

System 10 may also be modified to permit its use shipboard, on a boat, or in a building or building basement as a bilge or sump pump. System 10 may also be modified to permit its use by handicapped persons who are wheelchair- or bed-bound. Switch or control 215, for example, may be a proximity sensor or motion sensor, or may be configured to detect a user's eye motions and respond accordingly thereto. Indeed, system 10 can be configured to operate in conjunction with any device requiring on/off burst operation for the delivery of a fluid, and can be configured to enable remote control of devices where wires can be difficult or dangerous to employ.

Upon having and understood the present specification and drawings, those skilled in the art will understand that at least some of the various embodiments disclosed and described herein solve certain problems and provide certain solutions not existing in the prior art, such as: (a) providing a portable hydration system where a user interface or a fluid reservoir/pump/control assembly can be uniquely paired to one or multiple users; (b) providing hydration to a user using wireless control in an essentially hands-free and non-distracting manner; (c) wirelessly controlling a hydration system and not requiring regular manual manipulation of a hydration hose or nozzle (and therefore not requiring a user to let go of a steering wheel or handlebar; (d) permitting multiple users to share the same vehicle but use their own wirelessly-controlled hydration packs; (e) permitting a user to easily adjust the operational parameters of a hydration system; (f) permitting a user of a wireless hydration system to employ multiple communication channels to avoid cross-talk and interference with other wireless devices; (g) permitting a user to select wireless communication channels; (h) permitting a hydration system to operate over a range of electrical voltages and with different types of power supplies; (h) providing on-board diagnostics to a user regarding, for example, the performance parameters of a hydration system; (i) providing a hydration system with on-board surge and EMI protection.

The above-described embodiments should be considered as examples of the invention, rather than as limiting its scope. In addition to the foregoing embodiments of the invention, review of the detailed description and accompanying drawings will show that there are many other embodiments of the invention. Accordingly, many combinations, permutations, variations and modifications of the foregoing embodiments of the various embodiments of the invention not set forth explicitly herein will nevertheless fall within the scope of such various embodiments. For example, and as described above, the various embodiments of the invention are not limited to means and methods for providing drinkable fluids to a user, and my instead be used to pump fluids from a bilge or a sump, or to otherwise controllably transfer fluid from one location to another.

I claim:

1. A method of pairing a plurality of first portable control systems with a second control system in a wirelessly-controlled and activated hydration system configured for use by a plurality of users, each of the first control systems comprising a first control assembly comprising a first wireless transceiver and at least a first computing device, the first computing device comprising at least a first non-transitory computer readable medium configured to store first instructions executable by at least a first processor, the second control system being separate from each of the first control systems and being configured for mounting on one or more of a vehicle, motorcycle and a bicycle, the second control system comprising a second control assembly comprising a user interface, a second wireless transceiver configured to transmit user control signals to the first wireless transceiver corresponding to one or more inputs provided to the user interface by a user included among the plurality of users, and at least a second computing device operably connected to the user interface and the second wireless transceiver, the second computing device comprising at least a second non-transitory computer readable medium configured to store second instructions executable by at least a second processor, the second non-transitory computer readable medium having a unique identification code stored therein, each of the first assemblies being configured for operable connection to and control of a corresponding fluid pump, wherein the first transceivers of the first control assemblies and the second wireless transceiver are together configured to permit the first and second control assemblies to communicate wirelessly with one another and to pair with one another, the method comprising:

selecting a wireless communication frequency from among a plurality of available wireless communication frequencies;

transmitting the unique identification code and the selected wireless frequency from the second transceiver to the first transceivers;

pairing each of the plurality of first control assemblies and the second control assembly to one another thereby to prevent crosstalk or interference between the first control systems and the second control system and other undesired nearby wirelessly communicating devices;

executing the first instructions in the first processor in each of the first control assemblies such that the first instructions include one or more of pump control instructions or portions thereof, pump on instructions, pump off instructions, pump rate instructions, pump duration instructions, pump rate instructions, and pump pulse width modulation instructions;

executing the second instructions in the second processor such that the second instructions include one or more of user control instructions or portions thereof, pump on instructions, pump off instructions, pump rate instructions, pump duration instructions, and pump pulse width modulation instructions, and configuring one of the first control assemblies to control one or more of a pressure at which fluid is delivered by the pump, a rate at which fluid is delivered by the pump, and a duration of time over which fluid is delivered by the pump when the user interface of the second control assembly is actuated by the user.

2. The method of claim 1, further comprising confirming successful unique pairing of the second control system with each of the first control systems.

3. The method of claim 1, further comprising confirming successful unique pairing of any of the first control systems with the second control system.

4. The method of claim 1, further comprising configuring an on-board potentiometer to control one or more of a pressure at which fluid is delivered by the pump, a rate at which fluid is delivered by the pump, and a duration of time over which fluid is delivered by the pump when the user interface of the second control assembly is actuated by the user.

5. The method of claim 1, further comprising configuring the second control assembly to send repeated pump-on commands to one or more the first control assembly for a predetermined period of time after the user interface has been pressed.

6. The method of claim 1, further comprising configuring each of the first control assemblies to repeat listening commands for a predetermined period of time after the user interface has been pressed.

7. The method of claim 1, further comprising providing the user interface of the second control assembly as a generating the unique identification code in the second control assembly.

8. The method of claim 1, further comprising providing one or more of a microprocessor, a controller, a microcontroller, and a central processing unit as the first processor in each of the first control assemblies or the second processor in the second control assembly.

9. The method of claim 1, further comprising configuring at least one of the plurality of first and second control assemblies to enter a power-saving sleep mode after a predetermined period of time has passed with no user inputs or activity.

10. The method of claim 1, further comprising configuring at least one of the first and second control assemblies to wake up from the power-saving sleep mode when the user provides an input to the user interface or initiates a power reset in the first or second control assemblies.

11. The method of claim 1, further comprising operably connecting one or more light emitting diodes (LEDs) to at least one of the first and second control assemblies, the one or more LEDs being configured to provide the user with visual feedback and information regarding control assembly pairing status, pairing signal strength, and power status.

12. The method of claim 1, further comprising locating the user interface separate from the second control assembly, the user interface and second control assembly being operably connectable.

13. The method of claim 12, further comprising attaching the separate user interface to a one of a handlebar, a component of a vehicle, the user's belt, wrist, glove, mitten, finger ring, clothing, sleeve, ski pole, or other portable or wearable device or clothing article.

14. The method of claim 1, further comprising multiple users serially using the user interface, the user interface being installed in or on a single vehicle or single bicycle, each user having its own first control assembly.

15. The method of claim 1, further comprising pairing the second control assembly uniquely to a plurality of first control assemblies.

16. The method of claim 1, further comprising bi-directionally communicating between transceivers located in first and second control assemblies.

17. The method of claim 1, further comprising operably connecting portable hydration systems to at least some of the first control assemblies, where the user interface or the fluid pump can be uniquely paired to a plurality of first control assemblies.

* * * * *